US010524664B2

(12) United States Patent
Liu et al.

(10) Patent No.: US 10,524,664 B2
(45) Date of Patent: Jan. 7, 2020

(54) DEVICES, METHODS, AND SYSTEMS OF FUNCTIONAL OPTICAL COHERENCE TOMOGRAPHY

(71) Applicant: Northwestern University, Evanston, IL (US)

(72) Inventors: Wenzhong Liu, Evanston, IL (US); Lian Duan, Evanston, IL (US); Hao F. Zhang, Deerfield, IL (US); Kieren J. Patel, Santa Monica, CA (US); Hao Li, Evanston, IL (US); Biqin Dong, Evanston, IL (US); Amani A. Fawzi, Chicago, IL (US)

(73) Assignees: NORTHWESTERN UNIVERSITY, Evanston, IL (US); OPTICENT, INC., Deerfield, IL (US)

( * ) Notice: Subject to any disclaimer, the term of this patent is extended or adjusted under 35 U.S.C. 154(b) by 227 days.

(21) Appl. No.: 15/583,615

(22) Filed: May 1, 2017

(65) Prior Publication Data

US 2018/0020922 A1    Jan. 25, 2018

Related U.S. Application Data

(60) Provisional application No. 62/329,849, filed on Apr. 29, 2016, provisional application No. 62/329,853, filed on Apr. 29, 2016.

(51) Int. Cl.
*G06T 7/00* (2017.01)
*A61B 5/00* (2006.01)
*A61B 5/145* (2006.01)

(52) U.S. Cl.
CPC .......... *A61B 5/0066* (2013.01); *A61B 5/0035* (2013.01); *A61B 5/145* (2013.01);
(Continued)

(58) Field of Classification Search
None
See application file for complete search history.

(56) References Cited

U.S. PATENT DOCUMENTS

| 6,549,801 B1* | 4/2003 | Chen | A61B 5/0073 250/350 |
| 2014/0268163 A1* | 9/2014 | Milner | A61B 3/102 356/451 |

OTHER PUBLICATIONS

United States Patent and Trademark Office, "Restriction Requirement," issued in connection with U.S. Appl. No. 15/584,018, dated Nov. 2, 2018, 7 pages.

(Continued)

*Primary Examiner* — William R Alexander
*Assistant Examiner* — Gary W O'Neill
(74) *Attorney, Agent, or Firm* — Leydig, Voit & Mayer, Ltd.

(57) ABSTRACT

The present disclosure provides systems and methods for the determining a rate of change of one or more analyte concentrations in a target using non invasive non contact imaging techniques such as OCT. Generally, OCT data is acquired and optical information is extracted from OCT scans to quantitatively determine a flow rate of fluid in the target; angiography is also performed using one or more fast scanning methods to determine a concentration of one or more analytes. Both calculations can provide a means to determine a change in rate of an analyte over time. Example methods and systems of the disclosure may be used in assessing metabolism of a tissue, where oxygen is the analyte detected, or other functional states, and be generally used for the diagnosis, monitoring and treatment of disease.

19 Claims, 27 Drawing Sheets

(52) U.S. Cl.
CPC ............ *A61B 5/489* (2013.01); *G06T 7/0012* (2013.01); *G06T 2207/10016* (2013.01); *G06T 2207/10101* (2013.01); *G06T 2207/30104* (2013.01)

(56) References Cited

OTHER PUBLICATIONS

Basché et al., "Single-Molecule Optical Detection, Imaging and Spectroscopy", 2007: VCH Verlagsgesellschaft mbH, 15 pages.
Yokota et al., "Spin-stretching of DNA and Protein Molecules for Detection by Fluorescence and Atomic Force Microscopy," Analytical Chemistry 71, 4418-4422 (1999), 5 pages.
Chen et al., "Lattice light-sheet microscopy: Imaging molecules to embryos at high spatiotemporal resolution", Science 346, 439, (2014), 14 pages.
Moerner, "Single-molecule chemistry and biology special feature: New directions in single-molecule imaging and analysis", (vol. 104, No. 39), Proceedings of the National Academy of Sciences of the United States of America, Sep. 25, 2007, 8 pages.
Ellis et al., "Cell biology—Join the crowd", Sep. 4, 2003, published on www.nature.com/nature, vol. 425, 27-28 (2003), 2 pages.
Manley et al., High-density mapping of single-molecule trajectories with photoactivated localization microscopy, published online: Nature Publishing Group http://www.nature.com/naturemethods, (2008), 3 pages.
Zhang et al.,"Ultrahigh-throughput single-molecule spectroscopy and spectrally resolved super-resolution microscopy", published online Aug. 17, 2015, Nature Methods, vol. 12, No. 10, Oct. 2015, 6 pages.
Jing et al., "Chemical Tags for Labeling Proteins Inside Living Cells,", Published on Accounts of Chemical Research 44, 784-792, vol. 44, No. 9, published on the Web on Aug. 31, 2011, www.pubs.acs.org/accounts, 9 pages.
Mlodzianoski et al., "Super-Resolution Imaging of Molecular Emission Spectra and Single Molecule Spectral Fluctuations", Mar. 22, 2016, Plos One, 2016. 11(3), 12 pages.
Dong et al., "Super-resolution spectroscopic microscopy via photon localization", Nature Communications, published on Jul. 25, 2016, 8 pages.
Lelek et al., "Superresolution imaging of HIV in infected cells with FIAsH-PALM", published on www.pnas.org/cgi/doi/10.1073/pnas.1013267109, May 29, 2012, vol. 109, No. 22, 6 pages.
Hiraoka et al., "Multispectral imaging fluorescence microscopy for living cells", Cell Structure and Function, (2002) 27(5): 8 pages.
Yushchenko et al. "Tailoring Fluorescent Labels for Far-Field Nanoscopy", Springer (2012), 30 pages.
Levenson et al.,"Multispectral Imaging in Biology and Medicine: Slices of Life", Cytometry Part A, (2006) 69a(8): 11 pages.
Min et al., "Coherent Nonlinear Optical Imaging: Beyond Fluorescence Microscopy", in Annual Review of Physical Chemistry, vol. 62, S. R. Leone, P. S. Cremer, J. T. Groves, and M. A. Johnson, eds. (2011), 27 pages.
Gould et al., "Nanoscale imaging of molecular positions and anisotropies", Nature Methods, (2008) 5(12): 4 pages.
Walker et al., "Quantification of immunohistochemistry—issues concerning methods, utility and semiquantitative assessment I", Histopathology 49, 406-410 (2006), 5 pages.
Dunn et al., "A practical guide to evaluating colocalization in biological microscopy," American Journal of Physiology-Cell Physiology 300, C723-C742 (2011), 20 pages.
Dong et al., "Superresolution intrinsic fluorescence imaging of chromatin utilizing native, unmodified nucleic acids for contrast," Proceedings of the National Academy of Science, Aug. 30, 2016, 6 pages.
Urban et al., "Subsurface Super-resolution Imaging of Unstained Polymer Nanostructures," Scientific Reports, Jun. 29, 2016, 9 pages.
Dong et al., "Stochastic fluorescence switching of nucleic acids under visible light illumination," Optics Express 25, 7929-7944 (2017), 16 pages.
Le Gros et al., "X-ray tomography of whole cells," Current opinion in structural biology 15, 593-600, published on Sep. 8, 2005 (2005), 8 pages.
Razin et al., "Chromatin without the 30-nm fiber Constrained disorder instead of hierarchical folding," Epigenetics 9, 653-657, published on Feb. 21, 2014, 6 pages.
Tremethick, "Higher-order structures of Chromatin. The elusive 30 nm Fiber," Cell 128, Feb. 23, 2007, 4 pages.
Watanabe et al, "Wide-area scanner for high-speed atomic force microscopy," Review of Scientific Instruments 84 (2013), 11 pages.
Klar et al., "Fluorescence microscopy with diffraction resolution barrier broken by stimulated emission," www.pnas.org, Jul. 18, 2000, 5 pages.
Rust et al., "Sub-diffraction-limit imaging by stochastic optical reconstruction microscopy (STORM)," Natature Publishing Group, Oct. 2006, vol. 3, No. 10, 3 pages.
Betzig et al., "Imaging intracellular fluorescent proteins at nanometer resolution," downloaded from http://science.sciencemag.org/ on Jun. 9, 2017, 8 pages.
Vaya et al.,"Fluorescence of Natural DNA: From the Femtosecond to the Nanosecond Time Scales," Published on Web Aug. 10, 2010, J. Am. Chem. Soc. 9., vol. 132, No. 34, (2010), 2 pages.
Anders, "DNA Fluorescence at Room-Temperature Excited by Means of a Dye-Laser," Chemical Physics Letters vol. 81, No. 2 Jul. 15,1981, 3 pages.
Plessow et al., "Intrinsic time-and wavelength-resolved fluorescence of oligonucleotides: A systematic investigation using a novel picosecond laser approach," J Chemical Physics Letters 104, 3695-3704 Nov. 22, 1999, 10 pages.
Takaya et al., "UV excitation of single DNA and RNA strands produces high yields of exciplex states between two stacked bases," www.pnas.orgycgiydoiy10.1073ypnas.0802079105, Jul. 29, 2008, vol. 105, No. 5, 6 pages.
Bancaud et al., "A fractal model for nuclear organization. current evidence and biological implications," Nucleic Acids Research, vol. 40, No. 18, Nov. 2008, published online on Jul. 11, 2012, 10 pages.
Daban et al., "High concentration of DNA in condensed chromatin," Biochem. Cell Biol 81, 91-99 (2003), 9 pages.
Bohrmann et al., "Concentration evaluation of chromatin in unstained resinembedded sections by means of low-dose ratio-contrast imaging in STEM," Ultramicroscopy 49, 235-251 (1993), 17 pages.
Foelling et al., "Fluorescence nanoscopy by ground-state depletion and single-molecule return," Nature Methods 5, 943-945, published online on Sep. 15, 2008, 3 pages.
Burzykowski, "Analysis of photon count data from single-molecule fluorescence experiments," Chemical Physics, https://www.journals.elsevier.com/chemical-physics, (2003), 17 pages.
Boettiger et al., "Super-resolution imaging reveals distinct chromatin folding for different epigenetic states," Nature vol. 529, 418-422, Jan. 21, 2016, 15 pages.
Huang et al., "Three-dimensional super-resolution imaging by stochastic optical reconstruction microscopy,", published on Feb. 8, 2008, vol. 319, Science www.sciencemag.org, downloaded from http://science.sciencemag.org/ on Jun. 9, 2017, 5 pages.
Jones et al., "Fast, three-dimensional super-resolution imaging of live cells," Nature methods, vol. 8, Jun. 2011, published online May 8, 2011, 10 pages.
Dempsey et al., "Evaluation of fluorophores for optimal performance in localization-based super-resolution imaging," Nature Methods vol. 8, No. 12, Dec. 2011, 14 pages.
Levi et al., "Chromatin Dynamics in Interphase Cells Revealed by Tracking in a Two-Photon Excitation Microscope," Biophysical Journal, vol. 89, Dec. 2005, 11 pages.
Pfeiffer et al., "High-pressure freezing Provides New Information on Human Epidermis: Simultaneous Protein Antigen and Lamellar Lipid Structure Preservation. Study on Human Epidermis by Cryoimmobilization," Journal of Investigative Dermatology, vol. 114, No. 5, May 2000 , 9 pages.

(56) References Cited

OTHER PUBLICATIONS

Rostaing et al., "Preservation of immunoreactivity and Fine Structure of Adult C-elegans Tissues Using High-pressure freezing," Journal of Histochemistry & Cytochemistry, vol. 52, (2004) 12 pages.
Driel et al, "Tools for correlative cryo-fluorescence microscopy and cryo-electron tomography applied to whole mitochondria in human endothelial cells," European Journal of Cell Biology 88, 669-684 (2009), 16 pages.
Lu et al., "Single-molecule spectral fluctuations at room temperature," Letters to Nature, Jan. 9, 1997, vol. 385, 4 pages.
Ambrose et al, "Fluorescence Spectroscopy and Spectral Diffusion of Single Impurity Molecules in a Crystal," Letters to Nature vol. 349, Jan. 17, 1991, 3 pp.
Balzarotti et al, "Nanometer resolution imaging and tracking of fluorescent molecules with minimal photon fluxes," Science, Feb. 10, 2017, 8 pages.
Schmied et al, "DNA origami-based standards for quantitative fluorescence microscopy," Nature Protocols vol. 9, No. 6, published online May 15, 2014, 25 pages.
Roy et al, "Nanocytological Field Carcinogenesis Detection to Mitigate Overdiagnosis of Prostate Cancer: A Proof of Concept Study," Plos One, Feb. 23, 2015, 10 pages.
Kundukad et al., "Effect of YOYO-1 on the mechanical properties of DNA," Soft Matter 10, Published on Oct. 28, 201, 8 pages.
Buchvarov et al "Electronic energy delocalization and dissipation in single- and double-stranded DNA," Proceedings of the National Academy of Sciences of the United States of America, Mar. 20, 2007, vol. 104, No. 12, 4 pages.
Barbatti et al., "Photoinduced Phenomena in Nucleic Acids I", Topics in Current Chemistry, Springer (2015), 365 pages.
Blumberger, "Recent Advances in the Theory and Molecular Simulation of Biological Electron Transfer Reactions," Chemical Reviews 115, 11191-11238 (2015), 48 pages.
Hedegaard et al, "Spectral unmixing and clustering algorithms for assessment of single cells by Raman microscopic imaging," Theoretical Chemistry Accounts 130, 1249-1260 (2011), published on Jun. 7, 2011, 12 pages.
Ward Jr., "Hierarchical grouping to optimize an objective function," Journal of the American statistical association 58, 236-244 (1963), published online on Apr. 10, 2012, 10 pages.
MacQueen, "Some methods for classification and analysis of multivariate observations," in Proceedings of the fifth Berkeley symposium on mathematical statistics and probability(Oakland, Ca, USA 1967), pp.281-297, 17 pages.

Pearson, "On lines and planes of closest fit to systems of point in space," Philosophical Magazine 2, 559-572 (1901), 14 pages.
Hu et al, "Deep convolutional neural networks for hyperspectral image classification," Journal of Sensors, vol. 2015, 13 pages.
LeCun et al., "Gradient-based learning Applied to Document Recognition," Proceedings of the IEEE 86, 2278-2324 (1998), 47 pages.
Larsson et al., Characterization of the Binding of the Fluorescent Dyes YO and YOYO to DNA by Polarized-Light Spectroscopy. Journal of the American Chemical Society, 1994. 116(19): p. 8459-8465, 7 pages.
Cruz et al., "Quantitative nanoscale imaging of orientational order in biological filaments by polarized superresolution microscopy." Proceedings of the National Academy of Sciences of the United States of America, published online on Feb. 1, 2016. 113(7): p. E820-E828, 9 pages.
Backer et al, Enhanced DNA imaging using super-resolution microscopy and simultaneous single-molecule orientation measurements. Optica Society of America, Jun. 2016. vol. 3, No. 6: p. 659-666, 8 pages.
Ovesny et al., ThunderSTORM: a comprehensive ImageJ plug-in for PALM and STORM data analysis and super-resolution imaging. Bioinformatics, Apr. 25, 2014, vol. 30, No. 16, 2 pages.
Axelrod, "Carbocyanine Dye Orientation in Red-Cell Membrane Studied by Microscopic Fluorescence Polarization Biophysical Journal", Jun. 1979. vol. 26, No. 3, 17 pages.
Chen et al., "Polarization spectroscopy of single CdSe quantum rods" Physical Review B, vol. 64, No. 24, 2001, 4 pages.
Juette et al., "Single-molecule imaging of non-equilibrium molecular ensembles on the millisecond timescale" Nature Methods, Apr. 2016, vol. 13, No. 4, published online on Feb. 2016, 7 pages.
Vincent et al., "Application of Optical Coherence Tomography for Monitoring Changes in Cervicovaginal Epithelial Morphology in Macaques:Potential for Assessment of Microbicide Safety" Sexually Transmitted Diseases, Mar. 2008 vol. 35, No. 3, p. 269-275, 7 pages.
Gao et al., "Snapshot hyperspectral retinal camera with the Image Mapping Spectrometer (IMS)", Jan. 1, 2012, vol. 3, No. 1, Biomedical Optics Express 48, 7 Pages.
Vincent et al.,"High Resolution Imaging of Epithelial Injury in the Sheep Cervicovaginal Tract: A Promising Model for Testing Safety of Candidate Microbicides", Sexually Transmitted Diseases, vol. 36, No. 5, May 2009, 7 pages.
Johnson et al., "Snapshot hyperspectral imaging in ophthalmology", Journal of Biomedical Optics 12(1), 014036 (Jan./Feb. 2007), 7 pages.
Khoobehi, "A new snapshot hyperspectral imaging system to image optic nerve head tissue", Acta Ophthalmologica 2014, 1 page.

\* cited by examiner

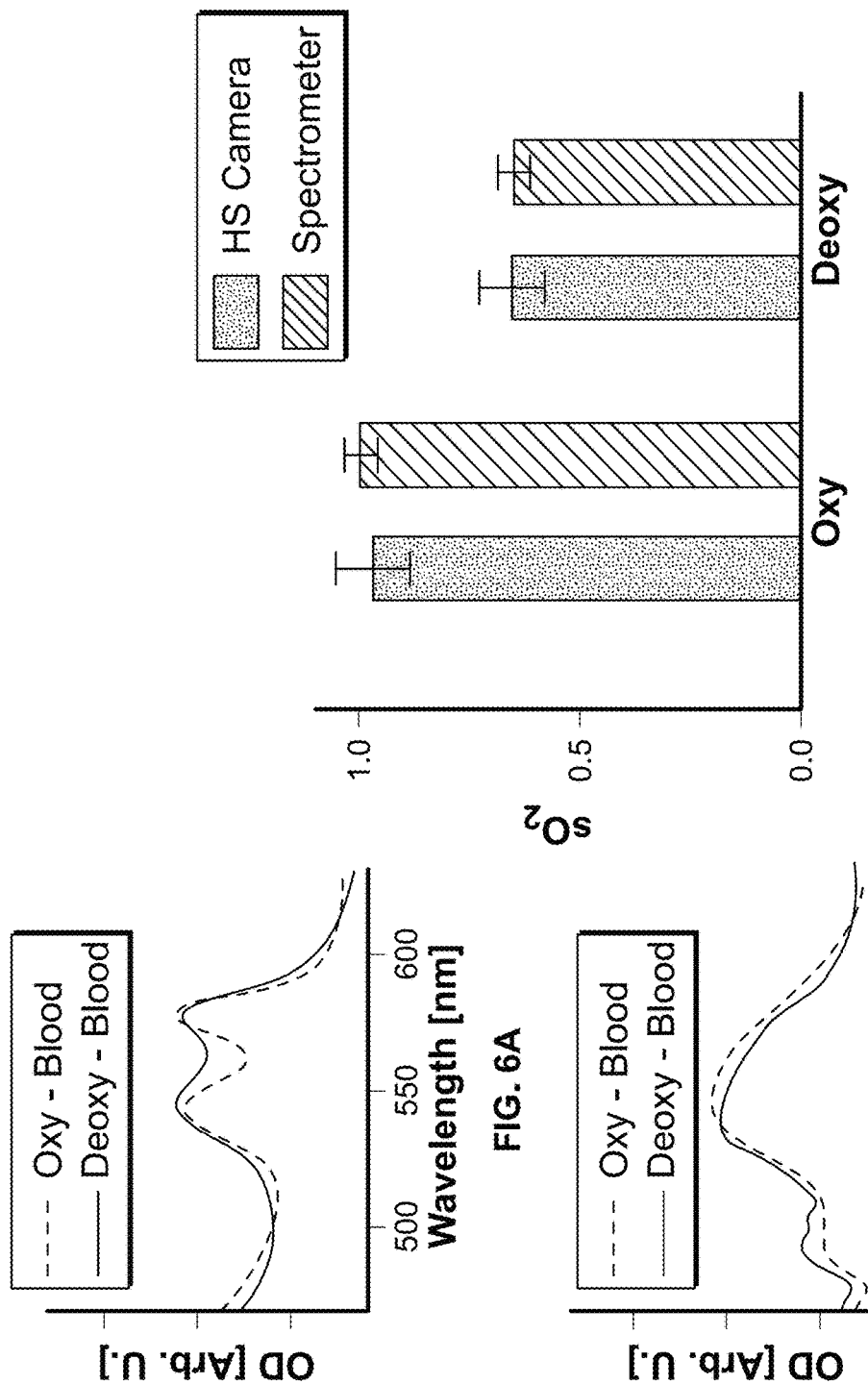

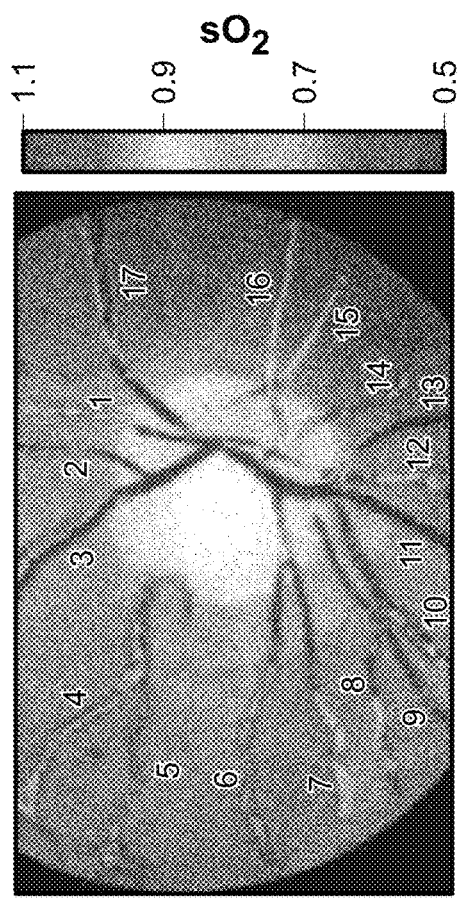
FIG. 14B
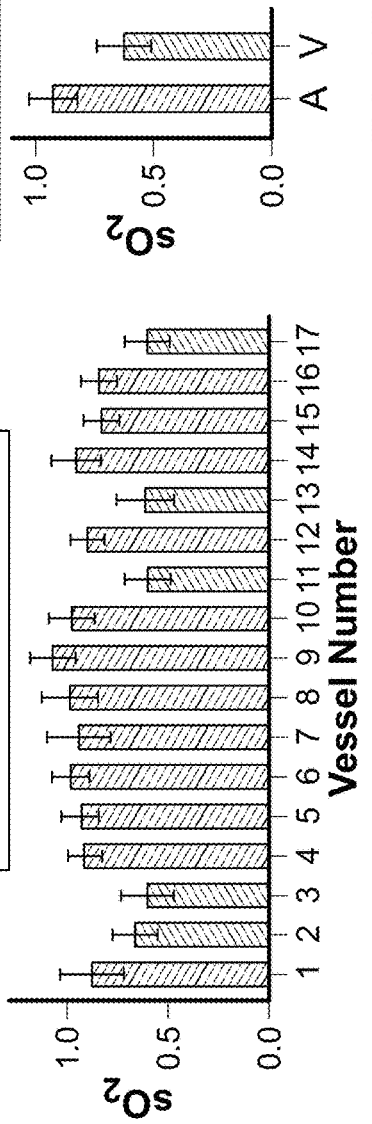
FIG. 14D
FIG. 14C

Probe 1

Probe 2

Bscan image of macaque vagina from probe 1
Enface image: 5mm by 5 mm
FIG. 21A
Epithelium →
Submucosa →
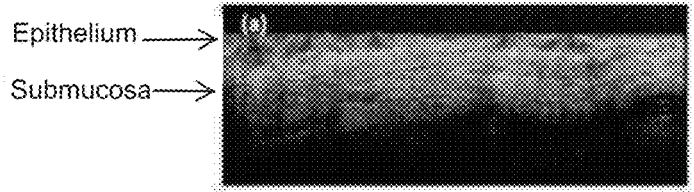
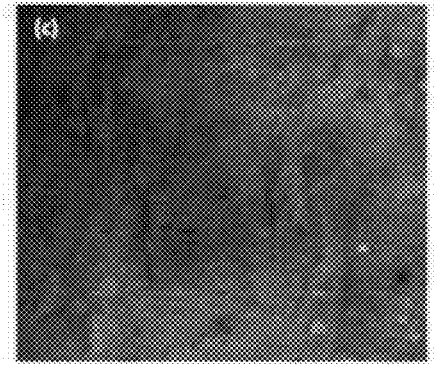
FIG. 21B
Epithelium →
Submucosa →
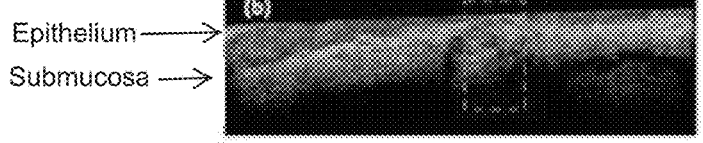
FIG. 21C

DEVICES, METHODS, AND SYSTEMS OF FUNCTIONAL OPTICAL COHERENCE TOMOGRAPHY

RELATED APPLICATIONS

This patent arises from U.S. Provisional Patent Application Ser. No. 62/329,853, which was filed on Apr. 29, 2016, and U.S. Provisional Patent Application Ser. No. 62/329,849, which was filed on Apr. 29, 2016. U.S. Patent Application Ser. No. 62/329,853 and U.S. Patent Application Ser. No. 62/329,849 are hereby incorporated herein by reference in their entirety.

STATEMENT REGARDING FEDERALLY SPONSORED RESEARCH FOR DEVELOPMENT

This invention was made with government support under R01 EY019951, and R24 EY022883 awarded by the National Institutes of Health and, CBET1055379, awarded by the National Science Foundation. The government has certain rights in the invention.

BACKGROUND OF THE DISCLOSURE

Optical Coherence Tomography (OCT) is a non-invasive optical imaging technique which produces depth-resolved reflectance imaging of samples through the use of a low coherence interferometer system. OCT imaging allows for three-dimensional (3D) visualization of structures in a variety of biological systems and non-biological systems not easily accessible through other imaging techniques. In some instances OCT may provide a non-invasive, non-contact means of assessing information without disturbing or injuring a target or sample. In medicine for example, OCT applications have included but are not limited to non-invasive means of diagnosis of diseases in the retina of the eye, interventional cardiology treatment and assessment, and diagnostics of skins lesion for dermatology.

Generally, OCT is used to generate 3D images of various structures, including vessels such as blood vasculature. Previously described methods of OCT provide methods for obtaining structural information directed at acquiring information about the size, shape, topology and physical attributes of the outside structures of vessels. However, information regarding physical and chemical attributes inside vessels and structures can also be useful, yielding more functional and potentially useful information about a system.

In medical diagnostics for example, vascular visualization and quantitative information about attributes of blood can be important for the diagnosis and treatment of many diseases. For example, approximately 50% of Americans will get cancer and approximately 50% of those will die from cancer. In the example of ocular disease, such as diabetic retinopathy, age related macular degeneration (AMD), glaucoma, nearly 10 million people in the U.S. and over 200 million people worldwide may be at risk for vision loss or blindness. It is suspected that vasculature remodeling and biochemical pathways that affect abnormal morphology of blood supplies in the eye and around tumors may be correlated with the onset and prognosis of these diseases, respectively. In some examples, an abnormal increase or decrease in metabolism, illustrated through abnormal blood vessel proliferation may also correlate with disease.

Non-invasive methods that allow acquisition of information about tissue attributes related to the etiologies of diseases, may lead to prevention of such diseases. The ability to measure blood flow, and other various biochemical analytes within a blood flow, such as oxygen (pO2), glucose or other biomarkers can help indicate a functional state of target tissue, such as metabolic activity. In some examples, the ability to understand a functional state of a target tissue, can be useful for treatment, monitoring or prevention of disease. This especially true when attributes such both as blood flow and oxygen can both be measured. Currently, there are no non-invasive three dimensional (3D) imaging techniques to measure oxygen metabolism in vivo in tissues. There is need in the art for improved methods and devices for non-invasive 3D quantitative imaging of metabolism and other target functions for a variety of applications including but not limited to the treatment and diagnosis of disease.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 6A-6B show example transmission spectra of oxygenated and deoxygenated blood.

FIG. 6C shows corresponding oxygen saturation levels for the transmission spectra of FIGS. 6A-6B.

FIGS. 14A-14D illustrates an example vessel calculation.

FIGS. 17-22 show example images and associated probes.

Figure 1A:
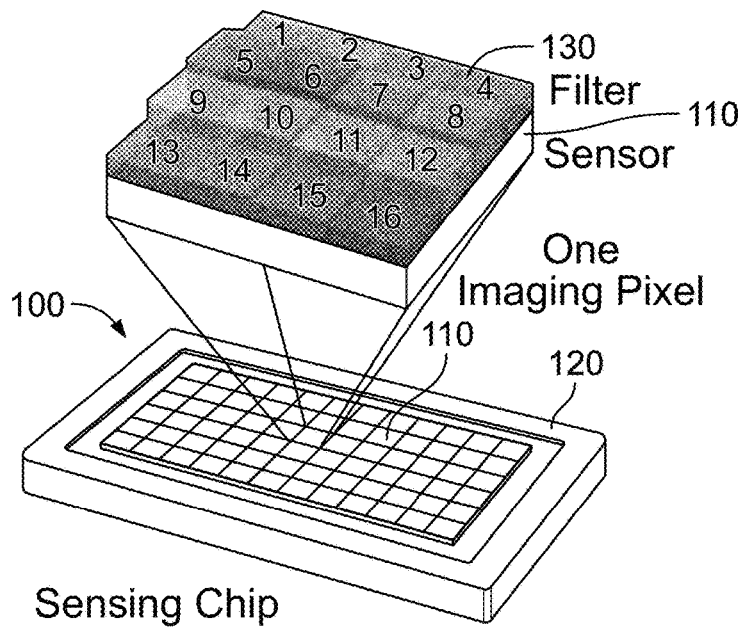
FIG. 1A illustrates an example spectral resolving detector array schematic.

The novel features of a device of this disclosure are set forth with particularity in the appended claims. A better understanding of the features and advantages of this disclosure will be obtained by reference to the following detailed description that sets forth illustrative examples, in which the principles of a device of this disclosure are utilized, and the accompanying drawings of which:

The following detailed description of certain examples of the present invention will be better understood when read in conjunction with the appended drawings. For the purpose of illustrating the invention, certain examples are shown in the drawings. It should be understood, however, that the present invention is not limited to the arrangements and instrumentality shown in the attached drawings.

DETAILED DESCRIPTION OF THE DISCLOSURE

Hyperspectral imaging resolves the light spectrum from each imaging pixel. It noninvasively reveals abundant retinal physiological and pathological information, which is useful for retinal disease diagnosis and therapeutic monitoring. However, most hyperspectral imagers either require long (>1 s) exposure time, which is sensitive to rapid eye movement, or use optical dispersive components to separate wavelength, which complicates the imaging system and makes their clinical application difficult.

Certain examples utilize a novel spectral resolving detector array (SRDA) and provide a compact, high-speed hyperspectral fundus camera. Certain examples achieve hyperspectral retinal imaging with 16 bands (470 to 630 nm) at 20 fps (frames per second). Certain examples also provide specific spectral recovery and analysis algorithms and demonstrated true-color recovery, false-color vessel contrast enhancement and retinal oxygen saturation ($sO_2$) mapping.

In certain examples, high-speed spectroscopic imaging can be applied to investigate $sO_2$ complications of retinal diseases such as diabetic retinopathy, age related macular degeneration, etc. Certain examples can be used to study melanin and lipofuscin related retinal diseases such as age related macular degeneration, etc. Certain examples can be used for portable hyperspectral imaging devices such as a handheld fundus camera, etc. Certain examples can be applied to real-time spectroscopic imaging technologies including real-time Raman microscopy and fluorescence imaging, etc.

Compared with existing hyperspectral retinal imagers, example systems and methods disclosed herein provide higher image speed (e.g., up to 340 fps). Such a high image speed greatly decreases image exposure time, reduces patient discomfort, and reduces spectral channel mis-registration under eye movement.

Certain examples provide cost-effective and easily implemented systems and methods. Certain examples involve no additional optics and can be equipped on a variety of imaging modalities through camera ports.

Certain examples relate to hyperspectral imaging, retinal imaging, retinal oxygen saturation, and retinal vessel contrast. In certain examples, three algorithms are disclosed to process hyperspectral image spectra: 1) reconstructing the spectra from relatively poor spectral resolution (e.g., 10 to 15 nm) and recover the image's true color; 2) composing false color with enhanced vessel-tissue color contrast; 3) accurately calculating $sO_2$ from hyperspectral image spectra.

The $sO_2$ calculation can be validated by ex vivo $sO_2$ measurement on bovine blood, for example. Calculated $sO_2$ from SRDA can be compared with $sO_2$ obtained from spectrometer measurements, for example. For example, an SRDA can be equipped on a home-built rodent fundus camera to image a Sprague Dawley rat retina in video rate (e.g., 20 fps). True color reconstruction, false-color vessel contrast enhancement and in vivo sO2 measurement can be performed as well.

While dispersive components can be used to separate wavelength and capture image and spectrum in one shot, the dispersers used with relay lens groups can double or even triple the system size. Such optical complexity makes the whole instrument bulky, delicate and impairs the fundus camera adjustability. Another approach is to use a fiber bundle to deliver light from fundus camera into a spectrometer. In this design, the limited fiber channels restrict the pixel number to be less than 500. Certain examples provide snapshot hyperspectral retinal imaging using a compact spectral resolving detector array to alleviate concerns, constraints, and issues with these other approaches.

Certain examples provide new systems and methods of retinal imaging based on hyperspectral retinal imaging techniques. Hyperspectral retinal imaging resolves the light spectrum from each imaging pixel to noninvasively reveal abundant retinal physiological and pathological information, which is useful for retinal disease diagnosis and therapeutic monitoring. However, most hyperspectral imagers either require long (>1 s) exposure time, which is sensitive to rapid eye movement, or use optical dispersive components to separate wavelength, which complicates the imaging system and makes their clinical application difficult. Using a novel spectral resolving detector array (SRDA), a compact, high-speed hyperspectral fundus camera can be constructed to achieve hyperspectral retinal imaging with 16 color channels at a speed of up to 340 fps. Compared with the existing hyperspectral retinal imagers, certain examples greatly decrease image exposure time, reducing patient discomfort and minimizing image artifacts due to eye movement.

Spectral Resolving Detector Array (SRDA) Working Principle Examples

Figure 1B:
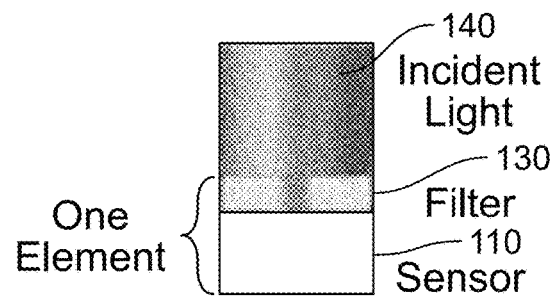
FIG. 1B illustrates an example spectral resolving principle.

In certain examples, a spectral resolved detector array (SRDA) (e.g., IMEC, Belgian) is fit onto a fundus camera. FIG. 1A shows an example detector array 100. The detector 100 is composed of 1024×2048 sensing elements 110 on an imaging chip 120 (e.g., Quartz Q-2A340, IMEC, Belgian; 5.5×5.5 μm element size, 340 fps (frames per second) maximum image speed), divided into 256×512 hyperspectral imaging pixels ("groups"). Each pixel has 4×4 elements, representing 16 wavelength channels, for example. For each sensing element 110, a dielectric-thin-film Fabry-Perot (FP) cavity filter 130 is monolithically fabricated on top of the sensor 110 (FIG. 1B). In the FP cavity, incident light 140 interferes with the reflection light, allowing only resonant wavelength (determined by film thickness) light to pass. The resonant wavelength is determined by the dielectric film thickness. 16 different filter thicknesses are assigned to the 16 channels, allowing light ranging from 470 to 630 nm to pass, for example.

In certain examples, a spectral response of 16 wavelength channels is characterized. A white diffusive tile (e.g., SphereOptics) is illuminated by a monochromatic light from a super-continuous light source (e.g., SC450, Fianium) and a monochromator (e.g., acousto-optic tunable filter, Fianium). The reflected light is collected and uniformly shined on the SRDA sensing chip 110 (e.g., 10 ms SRDA exposure time). The spectral response of each hyperspectral imaging pixel is recorded by sweeping the output wavelength of the monochromator. To block the second order transmission of FP cavities, the wavelength range can be restricted to 470-630 nm by adding a combination of a long-pass filter (e.g., OD4-450 nm, EdmundOptics) and a band-pass filter (e.g., BG-38 VIS, EdmundOptics), for example. The representative spectral responses of 16 channels are shown in the example of FIG. 1C.

Figure 1C:
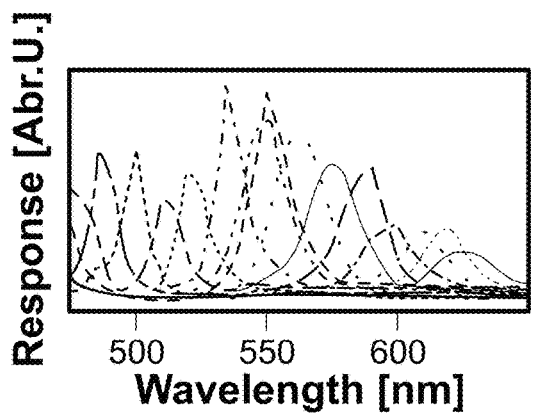
FIG. 1C illustrates an example spectral response.

As shown in the example of FIG. 1C, the 1 to 16 wavelength channel indices in one hyperspectral imaging pixel are labeled from upper-left to lower-right. In the example of FIG. 1C, the central wavelengths are 1: 534 nm; 2: 547 nm; 3: 522 nm; 4: 509 nm; 5: 624 nm; 6: 630 nm; 7: 607 nm; 8: 600 nm; 9: 578 nm; 10: 586 nm; 11: 562 nm; 12: 548 nm; 13: 485 nm; 14: 496 nm; 15: 474 nm; 16: 465 nm. In this example, the bandwidths are 10 to 15 nm. The quantum efficiency for each channel may not be even, which may be due to the fabrication process, for example.

Figure 2:
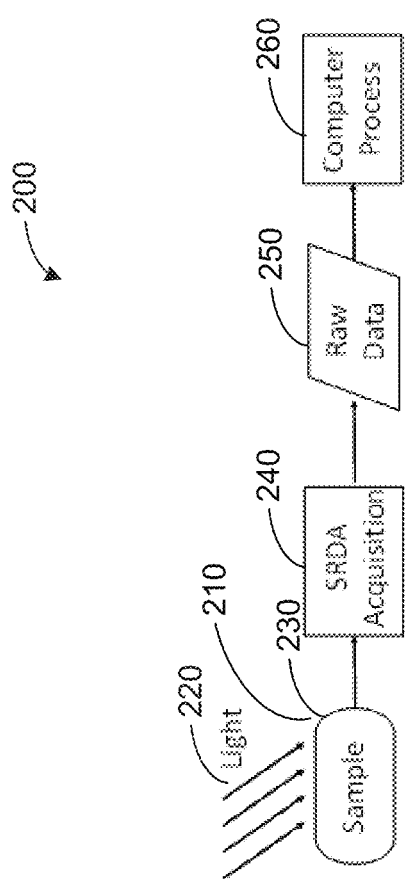
FIG. 2 illustrates an example imaging procedure.

An example imaging procedure is shown in FIG. 2. The example hyperspectral imaging acquisition method 200 of FIG. 2 begins at 210 with light 220 transmitted or reflected from one or more samples 230 to be imaged 240 on the SRDA sensing chip 100 through an appropriate imaging system (e.g., a microscope to image flat sample, a fundus camera for retinal imaging, etc.). The raw image data 250 is then transferred to a computer through a camera link. The date is then processed 260 through wavelength reconstruction to get hyperspectral images.

Example Spectral Analysis Algorithms

In certain examples, one or more spectral analysis algorithms can be applied to the image data.

Spectrum Reconstruction

In this example, raw data from SRDA is a 1024×2048 matrix. This matrix is divided into 256×512 groups with 4×4 elements in one group, for example, representing one hyperspectral imaging pixel. In spectral reconstruction, values in one group are assigned to different wavelength channels according to the wavelength calibration in FIG. 1C. To compensate the channel bandwidth and quantum efficiency, the values in each channel is divided by integration of the corresponding response spectrum.

True Color Recovery

In an example true color recovery, the spectrum of each pixel is projected to Red-Green-Blue (RGB) color space for color display. In certain examples, tristimulus values X, Y and Z are calculated by integrating the product of spectral and CIE 1931 XYZ color-matching functions. Then the tristimulus values are transferred from XYZ color space to RGB color space by inverse conversion matrix.

Vessel Color Contrast Enhancement and False Color Display

In this example, an 598 nm image channel minus 474 nm channel is selected as a blue channel, 549 nm minus 474 nm is selected as a green channel, and 474 nm image is selected as a red channel. Three channels are then displayed in RGB color space, for example. This arrangement aims to maximize the contrast difference between blood and tissue, and adjust the appearance of vessels in red and tissue in white.

sO$_2$ Calculation

Figure 3A:
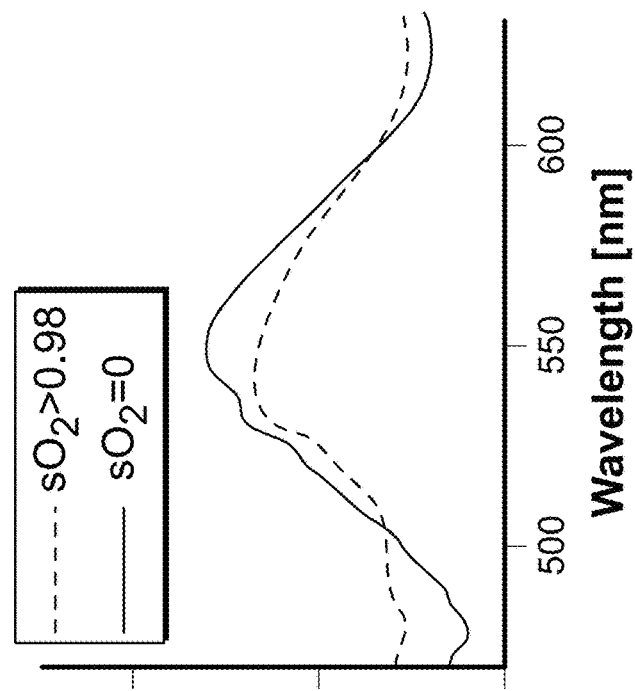
FIGS. 3A-3B show example blood attenuation coefficients for oxygen saturation calculation.
Figure 3B:
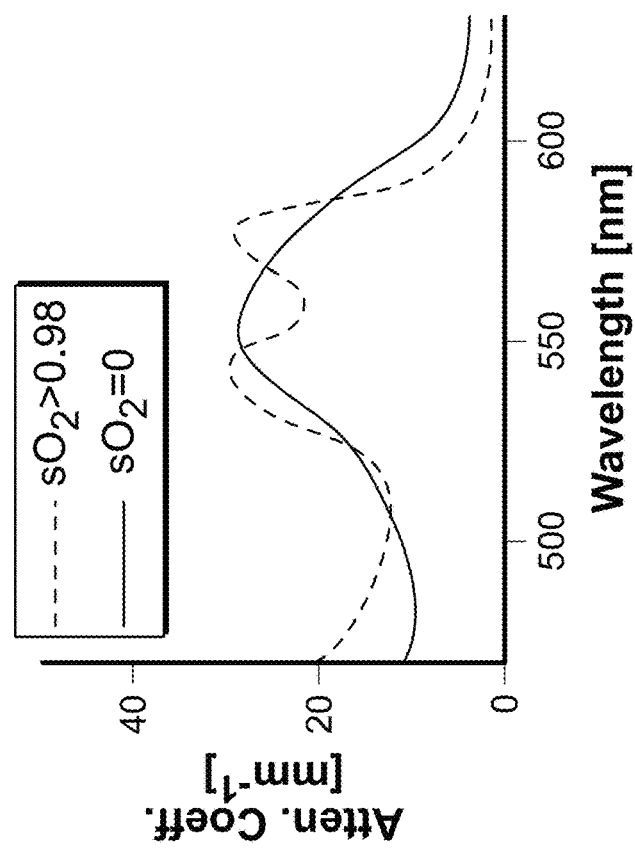

For an sO$_2$ calculation, the transmission spectra are converted to optical density (OD) spectra, and an sO$_2$ value is then calculated by least-square fitting OD spectra to the equation $$OD(\lambda) = B - N \ln(\lambda) + A[\mu_{HbR}(\lambda) + (1-sO_2)\mu_{HbO2}(\lambda)] \quad (1)$$

where B and N represent wavelength-independent and wavelength-dependent optical scattering, $\lambda$ is the optical wavelength; A is the product of experimental geometry factor and vessel diameter; $\mu_{HbR}(\lambda)$ and $\mu_{HbO2}(\lambda)$ are the fully deoxygenated and oxygenated blood effective attenuation coefficients convoluted with the SRDA spectral response (FIG. 3A: original effective attenuation coefficients showing standard whole blood effective attenuation coefficient spectra with hematocrit of 45%; FIG. 3B: convoluted coefficients indicating blood effective attenuation coefficient spectra convoluted with SRDA spectral response).

Ex Vivo sO$_2$ Measurement

Figure 4:
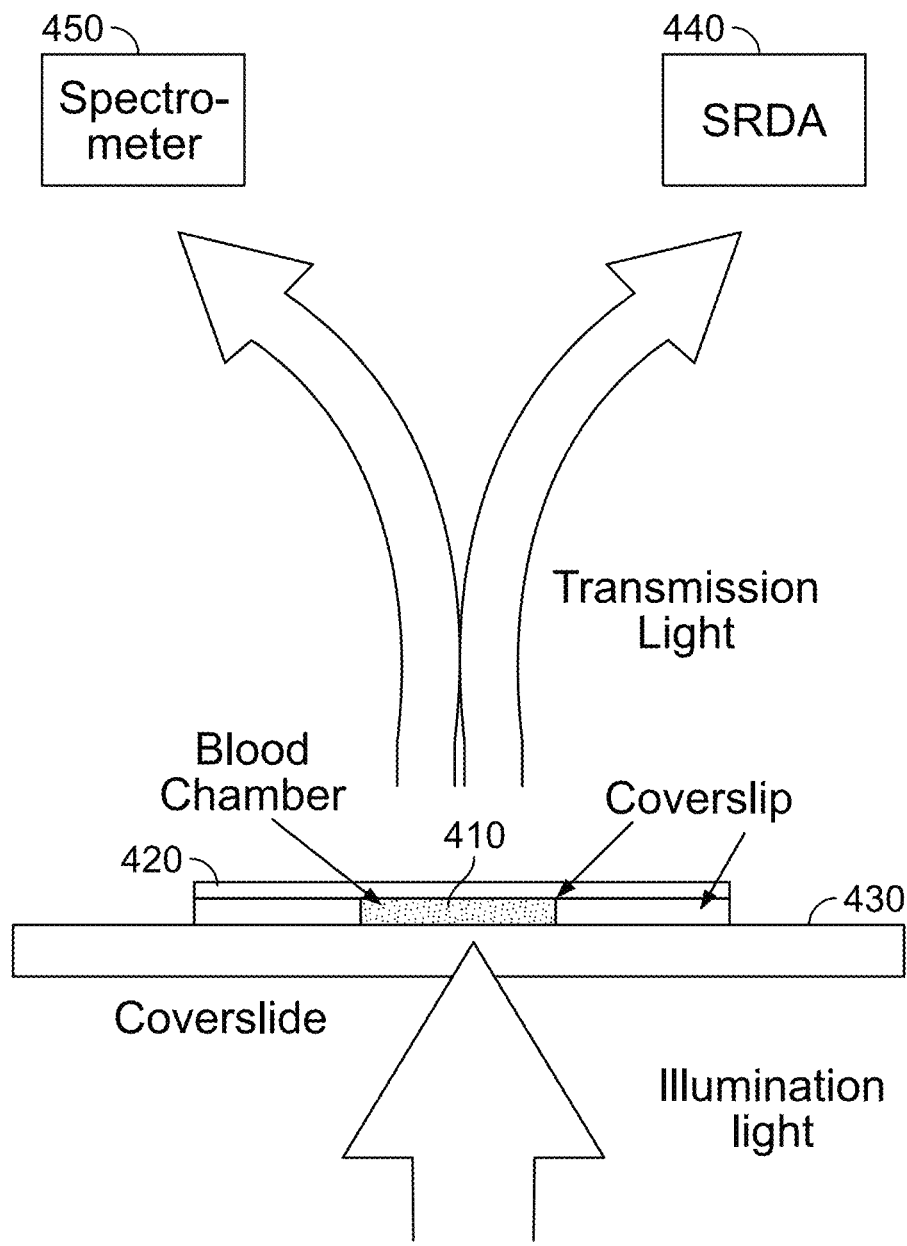
FIG. 4 shows an example schematic of a system for ex vivo oxygen saturation measurement.

In certain examples, oxygenated and deoxygenated blood samples can be prepared by exposing bovine blood (e.g., Quad Five Inc.) for one hour in air and pure nitrogen, respectively. As shown in the example of FIG. 4, blood samples can be added to a thin chamber 410 fabricated by glass coverslips 420 on a cover slide 430. In the illustrated example, the chamber thickness is 150 µm, determined by spacing coverslips 420. The chamber 410 can be placed under a microscope to capture the blood transmission spectra by SRDA 440 (e.g., 10 ms exposure time) and a spectrometer 450 successively, for example.

Fundus Camera

Figure 5:
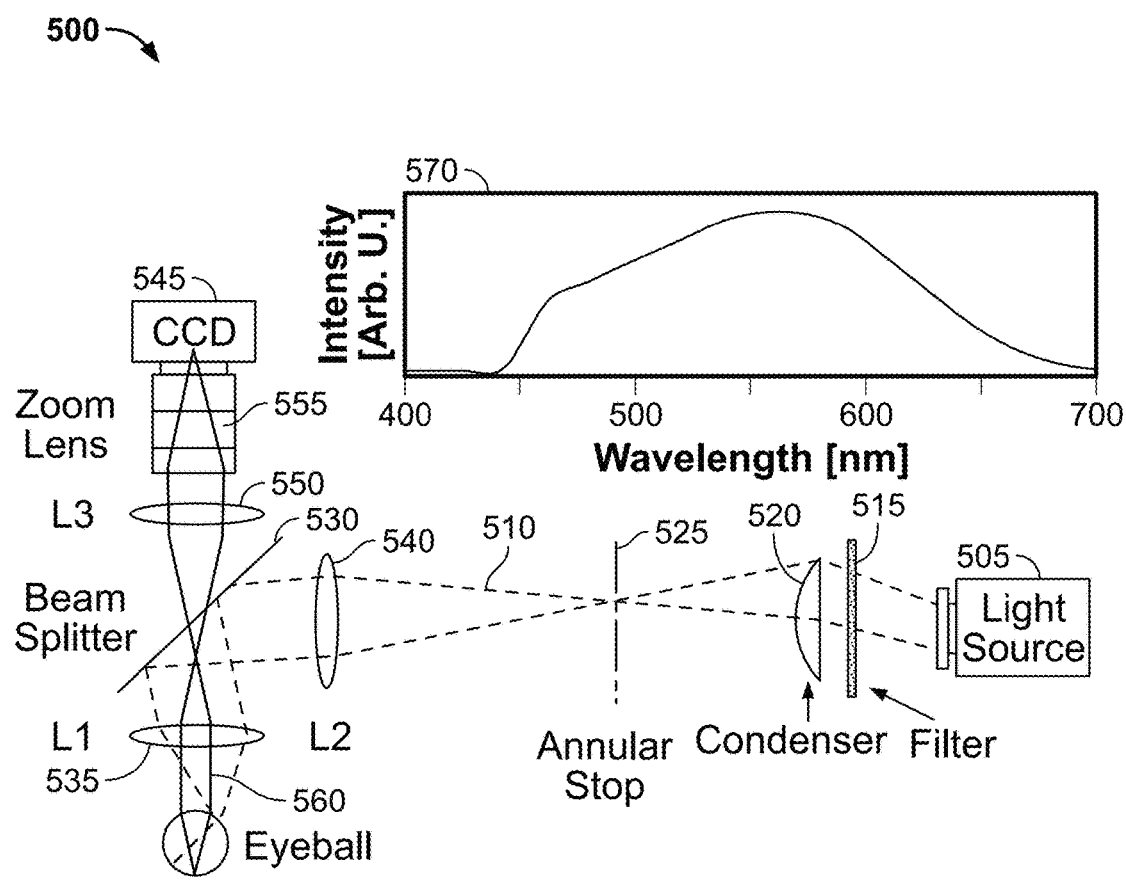
FIG. 5 shows an example hyperspectral fundus camera configuration.

An example hyperspectral fundus camera setup 500 is shown in FIG. 5. Using the system 500 of FIG. 5, illumination light from a light source 505, such as a halogen lamp, etc., is reshaped to a ring pattern and projected on an eyeball (e.g., a rat cornea, human cornea, etc.) (dashed line 510) using a filter 515, a condenser 520, an annular stop 525, a beam splitter 530, and a pair of lens 535, 540. The light reflected from the retina is collected to the SRDA 545 by an objective lens 550 and a zoom lens 555 (solid line 560). The fundus camera's field of view is about 50 degree, covering a retinal area of 5.6 mm in diameter, for example. The image resolution is about 20 µm, for example, limited by the pixel number of SRDA. The optical filters 515 can be added in front of the light (e.g., example illumination spectrum shown in the inset 570 in FIG. 5). Images can be taken under 20 fps with 45 ms exposure time, for example.

Example Ex Vivo sO$_2$ Measurements

The transmission spectra of oxygenated and deoxygenated blood obtained by spectrometer and SRDA (e.g., blood optical density measurements) are shown in FIG. 6A and FIG. 6B, respectively. Their corresponding sO$_2$ levels are shown in FIG. 6C (e.g., sO2 calculated by least-square fitting of optical density in FIGS. 6A-6B). In certain examples, due to the difference in wavelength resolution, SRDA cannot resolve fine spectral structures below 15 nm and the spectra looks different from spectrometer data. However, by fitting the convoluted attenuation spectra, sO$_2$ values calculated from SRDA are identical with that from spectrometer. In the example of FIGS. 6A-6C, the sO$_2$ levels for oxygenated and deoxygenated blood are 0.99 and 0.68 respectively (less than 3% difference between SRDA and spectrometer), for example, which is in the reasonable range. FIG. 6C shows FIG. 6C shows that by least-square fitting the convoluted hemoglobin attenuation spectra, sO$_2$ can be measured ex vivo by the SRDA as accurately as by spectrometer.

True Color Recovery

Figure 7A:
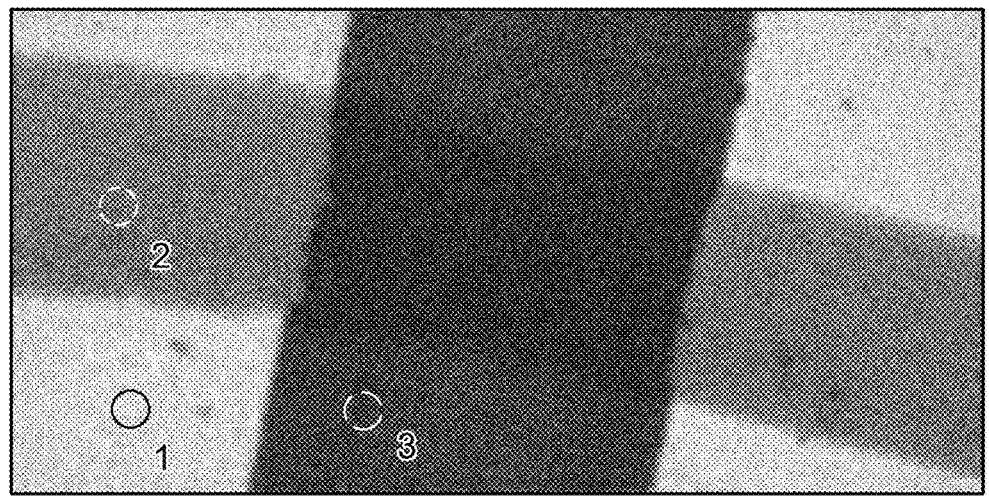
FIGS. 7A-7B show an example recovered true color image and representative spectra.
Figure 7B:
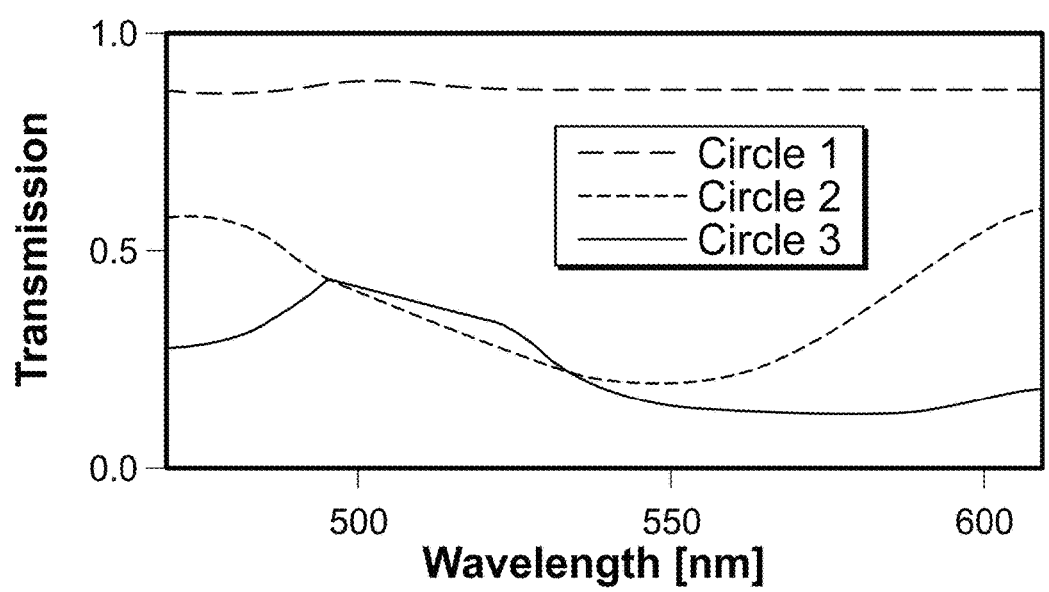

SRDA spectrum recovery can be verified by imaging a color cross pattern. A cross pattern can be drawn by red and blue markers on a cover slide, for example. Example recovered true color image and representative spectra are shown in FIG. 7A and FIG. 7B, respectively. The spectra clearly pointed out the absorption wavelengths region for different colors: red color absorbs more in short wavelength, blue absorbs more in long wavelength, and white color has a flat spectrum. The color image shows the red and blue lines, black cross section and white idle area, which is consistent with the actual color. FIG. 7B shows spectra corresponding to locations 1, 2, and 3 labeled in FIG. 7A.

True Color Retinal Image and False Color Vessel Contrast Enhancement

Figure 8A:
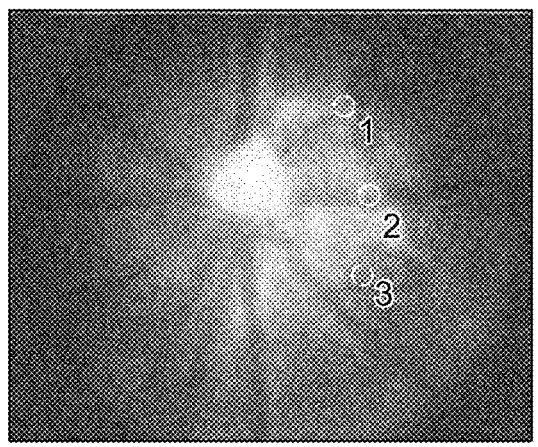
FIG. 8A shows an example true color retinal image reconstructed from spectra.

True color image shows the natural color of the subject as it appears to human eyes. True color is an important information of retinal photographs which helps ophthalmologists to evaluate eye diseases such as age-related macular degeneration. The true color retinal image reconstructed from spectra is shown in FIG. 8A. The overall color is yellowish due to the restricted illumination wavelength range. The arteries are light red and the veins are dark red, which is consistent with common color fundus images.

Figure 8C:
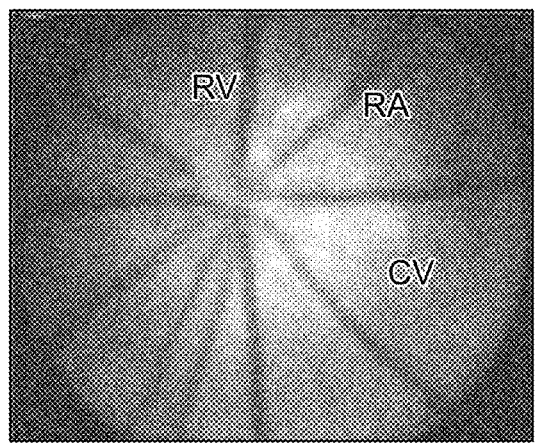
FIG. 8C shows a false color image with enhanced contrast between vessels and tissue.
Figure 8B:
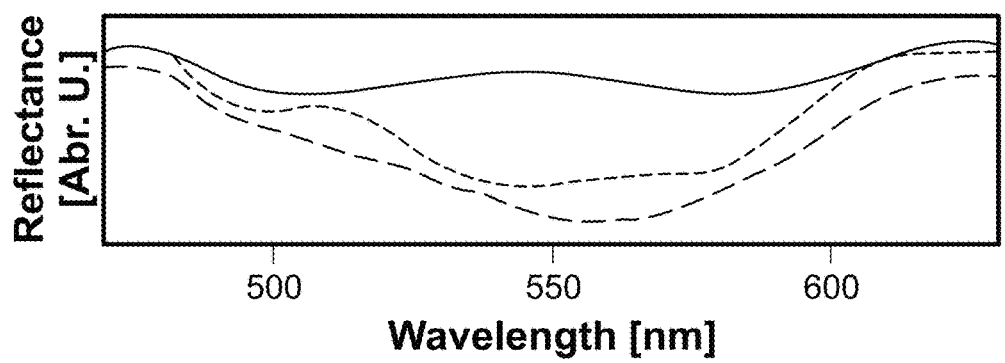
FIG. 8B shows representative reflection spectra of artery, vein and surrounding retinal area.

The representative reflection spectra of artery, vein and surrounding retinal area are shown in FIG. 8B. Artery and vein show different spectral signatures due to the different $sO_2$ values. The spectra signatures are closer to the convoluted hemoglobin absorption spectra in FIG. 3B rather than the original spectra in FIG. 3A due to the limited spectral resolution of SRDA. Surrounding retinal area has a relatively flat spectrum. Small spectral variation in surrounding area may due to the nerve fiber scattering or the unresolved small vessels.

Vessel contrast enhancement is a useful procedure in vascular visualization and segmentation. Spectral information from hyperspectral retinal image can be utilized to compose a false-color image with enhanced vessel-tissue color contrast. The false color retinal image is shown in FIG. 8C. Compared with the true color image in FIG. 8A, the false color clearly shows sharper retinal vessel color contrast. Some choroidal vessels hidden in the true color image are also visualized in the false color image.

Example In Vivo Retinal sO2 Measurement

Figure 9A:
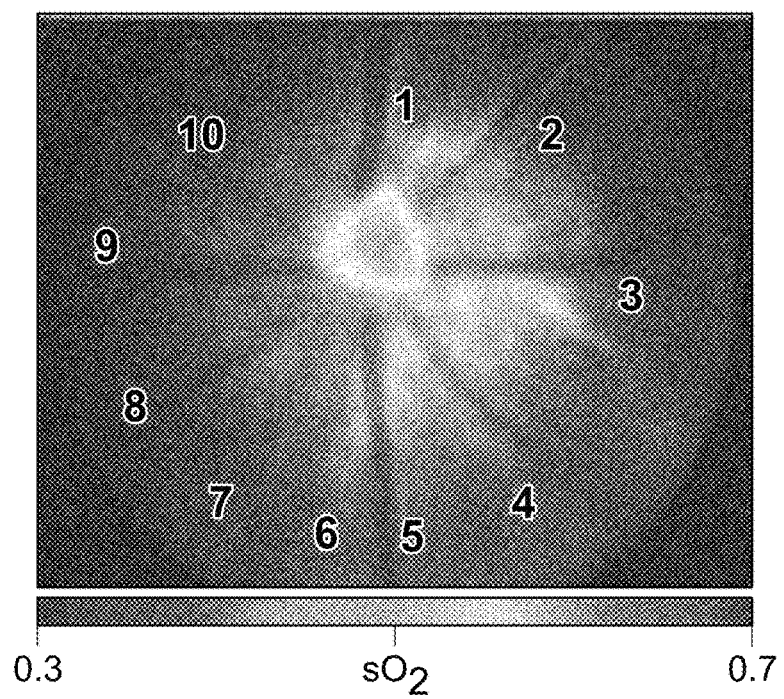
FIGS. 9A-9B show results of example in vivo retinal oxygen saturation measurement.
Figure 9B:
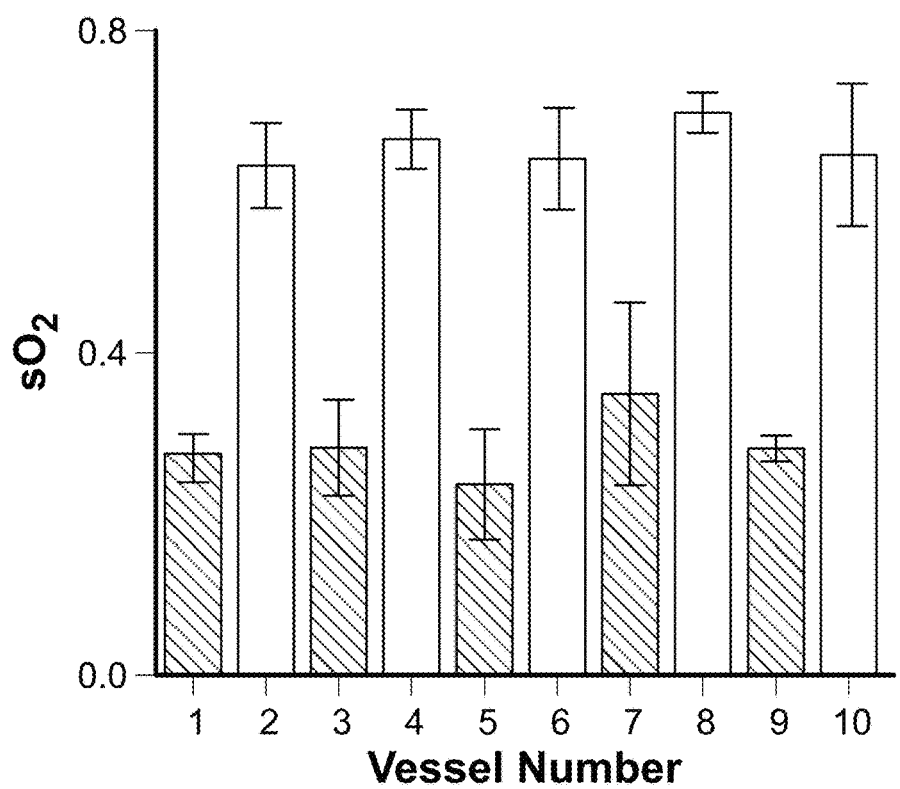
Figure 10:
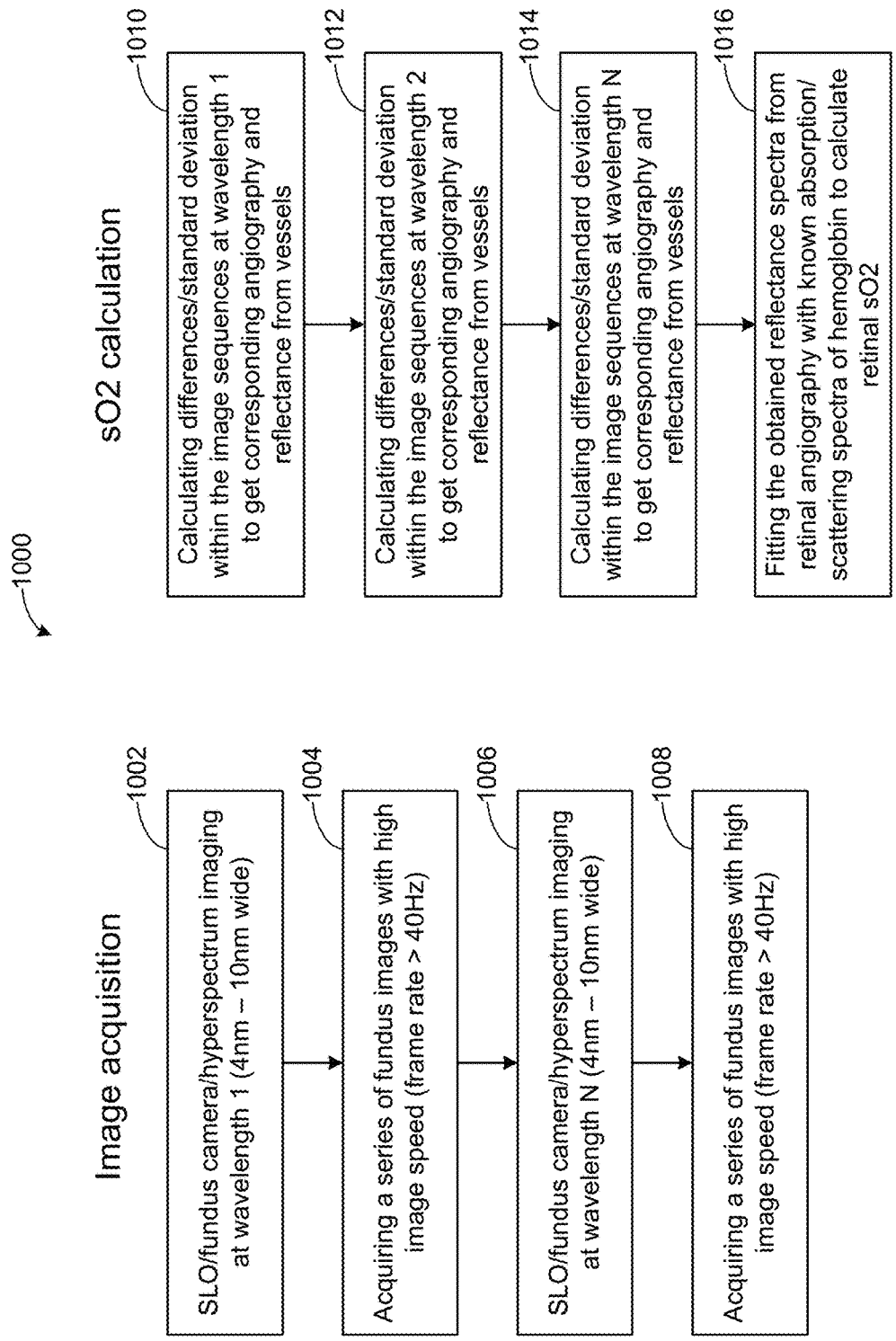
FIG. 10 illustrates a flow chart of an example method of oxygen saturation measurement based on fundus angiography.

Results of example in vivo retinal $sO_2$ measurement are shown in FIGS. 9A-9B. In this example, the blood vessel OD spectra are calculated by the equation $-\log_{10}(I_{in}/I_{out})$, where $I_{in}$ and $I_{out}$ are the spectra of vessel and the area adjacent to that vessel, respectively. OD spectrum is averaged for each vessel to minimize the spectral instability. $sO_2$ is calculated by least-square fitting OD spectra to Eq. 1 using attenuation spectra in FIG. 3B, for example. FIG. 9A shows the $sO_2$ map overlapped or fused with the retinal image (e.g., of main retinal vessels). The corresponding $sO_2$ values for individual vessels are shown in FIG. 9B. Arteries and veins show very distinct sO2 values as artery $sO_2$ values are averagely higher than vein's by 0.3, for example. However, the absolute values are lower than other retinal oximetry reports, where arteries $sO_2$ values should be close to 1 and vein $sO_2$ values should be around 0.6 to 0.7, for example.

sO2 Imaging Based on Angiography Contrast from Spectroscopic Fast Fundus Camera/Scanning Laser Ophthalmoscopy Traditional fundus camera, hyperspectral photography, scanning laser ophthalmoscopy (SLO) and so on detect light reflectance from retina to generate structural fundus images; by scanning across mulit wavelengths, these imaging devices can obtain retinal reflectance spectrum, which allows to measure functional information, like retinal sO2. The limitation, however, is that these sO2 measurements may be influenced by light scattering within retina as well as variation of local ocular geometrical parameters, such as vessel diameter. To further enhance the precision and stability of retinal sO2 measurement, fast imaging can be performed, acquiring a series of consequential images with narrow-band illumination (e.g., 4-10 nm) with high imaging speed (e.g., frame rate up to be 60 Hz). By taking a difference among these acquired image sequences, retinal vascular network information can be extracted. With retinal angiography, light reflectance can be preciseley detected directly from retinal vessels. By repeating this procedure across different wavelengths, a precise reflectance spectrum can be generated from retinal vessels, which benefits precise quantification of retinal sO2. The flow chart of retinal sO2 measurement based on fundus angiography is shown in FIG. 10.

For example, image acquisition begins at block 1002, with SLO/fundus camera/hyperspectrum imaging at a first wavelength (e.g., 4 nm-10 nm wide, etc.). At block 1004, a series of fundus images is acquired with high image speed (e.g., frame rate >40 Hz, etc.). At block 1006, SLO/fundus camera/hyperspectrum imaging is obtained at a second wavelength (e.g., 4 nm-10 nm wide, etc.). At block 1008, a series of fundus images is acquired with high image speed (e.g., frame rate <40 Hz, etc.).

Oxygen saturatino calculation begins at block 1010 by calculating differences/standard deviation within the image sequences at the first wavelength to obtain corresponding angiography and reflectance from vessels. At block 1012, differences/standard deviation within the image sequences are calculated at the second wavelength to obtain corresponding angiography and reflectance from vessels. At block 1014, differences/standard deviation within the image sequences are calculcated at an Nth wavelength to obtain corresponding angiography and reflectance from vessels. At block 1016, the obtained reflectance spectra from the retinal angiography are fit with known absorption/scattering spectra of hemoglobin to calculate retinal $sO_2$.

Figure 11:
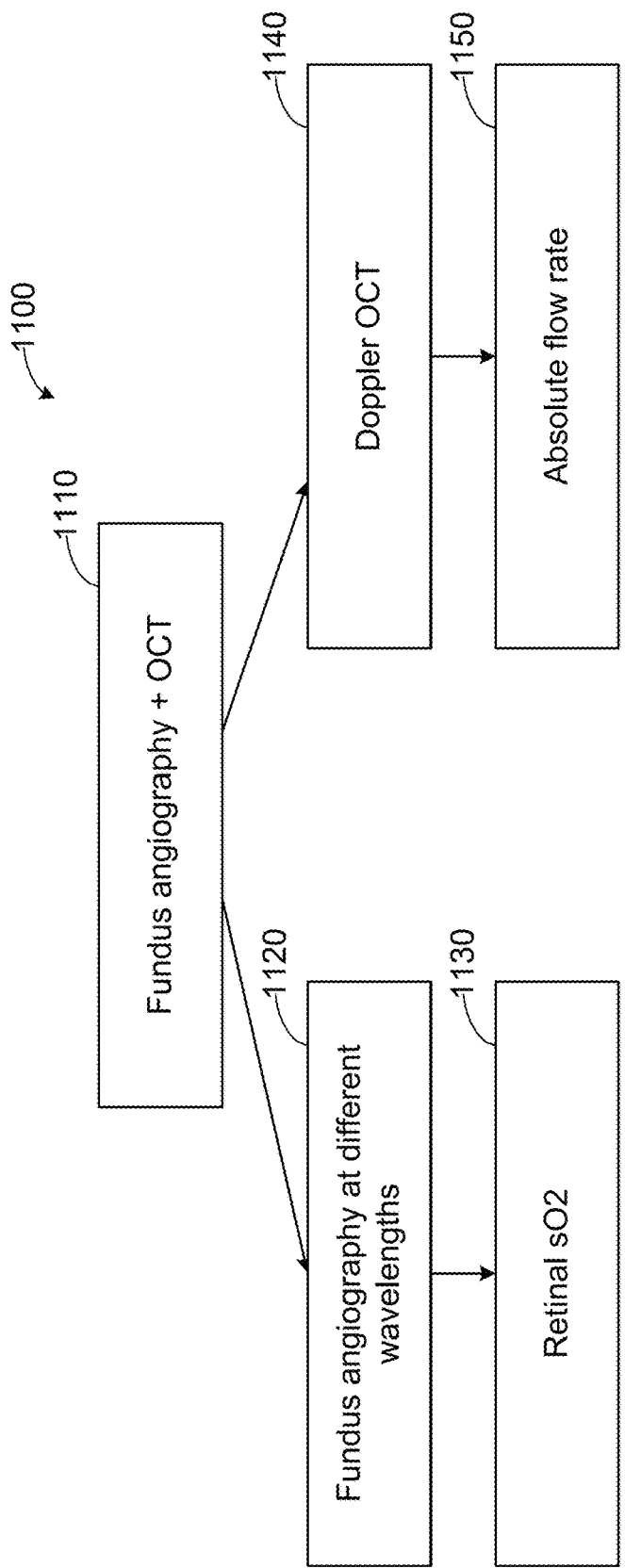
FIG. 11 illustrates a flow chart of an example method of combined fundus angiography and Doppler OCT for simultaneous retinal oxygen saturation and flow imaging.

Fundus angiography based retinal sO2 can be integrated with NIR Doppler OCT to simultaneously measure retinal blood sO2 and flow rate, thus measure retinal oxygen metabolic rate. The flow chart for simultaneous sO2 and flow measurement is shown in FIG. 11. FIG. 11 illustrates a flow chart of an example method of combined fundus angiography and Doppler OCT for simuntaneous retinal sO2 and flow imaging (1102). At block 1104, fundus angiography is determined at a plurality of wavelengths. Then, at block 1106, retinal $sO_2$ is calculated. At block 1108, Doppler OCT image data is obtained, and, at block 1110, an absolute flow rate is determined.

Terminology

The terminology used herein is for the purpose of describing particular examples only and is not intended to be limiting of a device of this disclosure. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Several aspects of a device of this disclosure are described above with reference to example applications for illustration. It should be understood that numerous specific details, relationships, and methods are set forth to provide a full understanding of a device. One having ordinary skill in the relevant art, however, will readily recognize that a device can be practiced without one or more of the specific details or with other methods. This disclosure is not limited by the illustrated ordering of acts or events, as some acts may occur in different orders and/or concurrently with other acts or events. Furthermore, not all illustrated acts or events are required to implement a methodology in accordance with this disclosure.

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another example. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

EXAMPLES

Example 1

Purpose: To validate the use of a novel spectral resolving detector array (SRDA) for high-speed hyperspectral retinal imaging in rodents, and the corresponding functional imaging capabilities including oxygen saturation rate ($sO_2$) measurements.

Methods: We equipped the SRDA on a home-built rodent fundus camera. We performed ex vivo $sO_2$ measurement on bovine blood by SRDA and compared the results with that from spectrometer measurements. We imaged the Sprague Dawley rat retina in video rate (20 fps). The true color reconstruction, false-color vessel contrast enhancement and in vivo $sO_2$ measurement were performed as well.

Results: We achieved hyperspectral retinal imaging with 16 bands (e.g., 470 to 630 nm) in video rate (e.g., 20 fps), for example. We enhanced the vessel-tissue color contrast from spectral analysis. The $sO_2$ values calculated from ex vivo SRDA measurements are consistent with that from spectrometer measurement (e.g., <3% deviation). In in vivo retinal vessel $sO_2$ measurements, the artery and vein $sO_2$ are around 0.7 and 0.35, for example, respectively. The overall $sO_2$ values offsets from the reasonable values by 0.3, for example.

Conclusions: Video-rate hyperspectral retinal imaging is achieved by SRDA. Useful spectral information is successfully provided for functional retinal imaging purpose including vessel-tissue color contrast enhancement and retinal $sO_2$ measurement.

Translational relevance: Our high-speed, compact hyperspectral imaging solution could bring hyperspectral retinal imaging from bench to bedside. Spectral information from hyperspectral images could help to analyze macular pigment absorption, retinal $sO_2$, and cell protein oxidative state, which are frequently involved in diabetic retinopathy, glaucoma and age-related macular degeneration.

Introduction

Hyperspectral imaging captures the light spectrum from every image pixel. Spectral analysis through hyperspectral images provides spectrally carried physiological and pathological information, which could be applied for disease diagnosis and surgical guidance. Hyperspectral imaging can be applied in fields such as oncology, cardiology, ophthalmology and dermatology.

Retinal diseases are often accompanied with retinal physiological changes and alter the light scattering and/or absorption properties of retinal tissues. Many important biomarkers are tightly related to reflection and absorption spectrum, including retinal vessel oxygen saturation rate ($sO_2$), macular pigment absorption and cell protein oxidative state. Hyperspectral retinal imaging has provided a noninvasive way to monitor those retinal biomarkers, and could potentially benefit diagnosis and therapeutic monitoring of several retinal diseases such as diabetic retinopathy, age-related macular degeneration and glaucoma.

Despite great advantages, clinical applications of hyperspectral retinal imaging has been limited by the time-consuming data acquisition or imaging system complexity. Traditionally, tunable optical filter or filter sets are used to separate light wavelength. Images of different wavelength are then registered to extract spectral information. Due to the need of filter tuning, one image stack takes several seconds to capture. Such a long exposure time not only raises patients' uncomfortableness, but also causes image artifacts from spectral channel mis-registration under eye movement.

Another approach is to use dispersive components to separate wavelength. In 2007, Johnson et al. integrated the 2-d grating disperser into a fundus camera and achieved snapshot retinal imaging with 50 bands from 450 nm to 700 nm, for example. In 2011, Liang et al. developed a snapshot hyperspectral technology using prism and lens arrays as disperser and achieved retinal imaging in 48 bands from 470 to 650 nm with 5.2 fps, for example. However, the dispersers along with relay lens groups doubled or even tripled the system size. Such optical complexity makes the whole instrument bulky, delicate and impairs the fundus camera adjustability. So far, a clinically applicable hyperspectral fundus camera with high speed, high resolution and compact design is yet to be developed.

In this work, we utilized a novel spectral resolving detector array (SRDA) and built a compact, high-speed and robust hyperspectral fundus camera for rats. We achieved 16-band (470 to 630 nm), 256×512-pixel hyperspectral imaging with 20 fps, for example. We also demonstrated true-color recovery, vessel contrast enhancement and retinal $sO_2$ measurement through spectral analysis. This work could bring hyperspectral retinal imaging from bench to bedside and also provided a solution for other hyperspectral imaging applications.

Methods

Spectral Resolving Detector Array

We used a SRDA prototype provided by IMEC, Belgian, for example. The schematic is shown in FIG. 1a. The 1024×2048 sensing elements on the imaging chip (Quartz Q-2A340, IMEC, Belgian; 5.5×5.5 μm element size, 340 fps maximum image speed) was divided into 256×512 hyperspectral imaging pixels, for example. Each pixel has 4×4 elements, representing 16 wavelength channels, for example. For each sensing element, a dielectric-thin-film Fabry-Perot (FP) cavity filter was monolithically fabricated on the top (FIG. 1B), for example. In the FP cavity, incident light interferes with the reflection light, allowing only resonant-wavelength light to pass. The resonant wavelength is determined by the dielectric film thickness. In our device, 16 different filter thicknesses are assigned to the 16 channels, allowing light ranging from 470 to 630 nm to pass, for example.

We characterized the spectral response of 16 wavelength channels. A white diffusive tile (e.g., SphereOptics) was illuminated by a monochromatic light from a super-continuous light source (e.g., SC450, Fianium) and a monochromator (e.g., acousto-optic tunable filter, Fianium). The reflected light was collected and uniformly shined on the SRDA sensing chip (e.g., 10 ms SRDA exposure time). The spectral response of each hyperspectral imaging pixel was recorded by sweeping the output wavelength of the monochromator. To block the second order transmission of FP cavities, we restricted the wavelength range to 470-630 nm by added a combination of a long-pass filter (e.g., OD4-450 nm, EdmundOptics) and a band-pass filter (e.g., BG-38 VIS, EdmundOptics), for example. The representative spectral responses of 16 channels are shown in FIG. 1c. The bandwidths are 10 to 15 nm, for example. The quantum efficiency for each channel is not even, which may due to the fabrication process. The bandwidth and quantum efficiency difference are balanced in spectrum recovery.

True Color Recovery

We verified the SRDA spectrum recovery by imaging a color cross pattern. The cross was drawn by red and blue markers on a cover slide. We installed the SRDA on a commercial microscope's camera port and applied the optical filter set described previously in front of the SRDA. The hyperspectral image was taken under transmission model with 10 ms exposure time, for example. The spectrum of each pixel is then projected to RGB color space for color display. Specifically, we first calculated the tristimulus values X, Y and Z by integrating the product of spectral and CIE 1931 XYZ color-matching functions, for example. The tristimulus values were then transferred from XYZ color space to RGB color space by inverse conversion matrix. The recovered true color image and the representative spectra are shown in FIGS. 8AD and 8B, respectively. The spectra clearly pointed out the absorption region for different color as red color absorbs more in short wavelength, blue absorbs more in long wavelength, and white color has a flat spectrum. The color image also shows the red and blue lines, black cross section and white idle area, which is consistent with the actual color.

Ex Vivo $sO_2$ Measurement

We further validated the SRDA sO2 measurement ex vivo by comparing the blood transmission spectral analysis between SRDA and spectrometer. We prepared oxygenated and deoxygenated blood samples by exposing bovine blood (e.g., Quad Five Inc.) for one hour in air and pure nitrogen, respectively.[17] As shown in FIG. 4, blood samples were added to a thin chamber fabricated by glass coverslips on a cover slide. The chamber thickness is 150 μm, determined by spacing coverslips, for example. We then put the chamber under a microscope (model) and captured the blood transmission spectra by SRDA (e.g., 10 ms exposure time) and a spectrometer (model, resolution) successively.

We used different algorithms to analyze spectrometer and SRDA data due to the different spectra resolution between these two methods. For spectrometer data analysis, we first converted the transmission spectra to optical density (OD) spectra, then calculated $sO_2$ value by least-square fitting OD spectra to the equation[18]

$$OD(\lambda)=B-N \ln(\lambda)+A[\mu_{HbR}(\lambda)+(1-sO_2)\mu_{HbO2}(\lambda)] \quad (1)$$

where B and N represent wavelength-independent and wavelength-dependent optical scattering, λ is the optical wavelength; A is the product of experimental geometry factor and vessel diameter; $\mu_{HbR}(\lambda)$ and $\mu_{HbO2}(\lambda)$ are the fully deoxygenated and oxygenated blood effective attenuation coefficients. For SRDA data, we convoluted $\mu_{HbR}(\lambda)$ and $\mu_{HbO2}(\lambda)$ with the SRDA spectral response. The convoluted spectra were then used as standard attenuation spectra for least-square fitting. The transmission spectra of oxygenated and deoxygenated blood obtained by spectrometer and SRDA are shown in FIG. 6A and FIG. 6B respectively. Their corresponding $sO_2$ levels are shown in FIG. 6C. Due to the difference in wavelength resolution, SRDA cannot resolve fine spectral structures below 15 nm, for example, and the spectra looks different from spectrometer data. However, by fitting the convoluted attenuation spectra, $sO_2$ values calculated from SRDA are identical with that from spectrometer. The $sO_2$ levels for oxygenated and deoxygenated blood are 0.99 and 0.68 respectively (less than 3% difference between SRDA and spectrometer), for example, which is in the reasonable range. From FIG. 6C, we can conclude that by least-square fitting the convoluted hemoglobin attenuation spectra, $sO_2$ can be measured ex vivo by the SRDA as accurately as by spectrometer.

Hyperspectral Fundus Camera

The hyperspectral fundus camera setup is shown in FIG. 5. Briefly, the illumination light from a halogen lamp was reshaped to a ring pattern and projected on the rat cornea (black dashed line). The light reflected from the retina was collected to the SRDA by an objective lens and a zoom lens (red solid line). The fundus camera's field of view is about 50 degree, covering a retinal area of 5.6 mm in diameter, for example. The image resolution is about 20 μm, limited by the pixel number of SRDA, for example. The optical filters were added in front of the light (illumination spectrum shown in the inset in FIG. 5). Images were taken under 20 fps with 45 ms exposure time, for example.

Animal Preparation

Sprague Dawley rats were used for in vivo retinal imaging. The animal preparation and operation are described in detail in our previous reports. Briefly, animals were anesthetized in an anesthesia chamber (2% isoflurane mixed with normal air at 3 liter/minute, 10 minutes), and the placed on a homemade animal holder for imaging (1.5% isoflurane at 2 liter/minute). The rat eyes were anesthetized by a drop of 0.5% Tetracaine Hydrochloride solution and dilated by a drop of 1% Tropicamide ophthalmic solution. During imaging, artificial tears were applied every other minute. All experiments were performed in compliance with the ARVO Statement for the Use of Animals in Ophthalmic and Vision Research, and were approved by the Animal Care and Use Committee of Northwestern University.

Results

In Vivo Hyperspectral Rat Retinal Imaging

Six wavelength channels of a raw rat retinal hyperspectral image can be obtained in an example. The obtained images clearly show the main retinal vessels and nerve fibers. Some small retinal vessels are vaguely seen. No choroidal vessel is resolved due to the strong absorption of RPE layer within the visible spectral range. Magnified images show that different channels are well co-registered. Contrast between vessels and surrounding tissues varies in different channels, e.g., the retinal vessels at 580 nm are darker than under other wavelength, showing a higher optical absorption, for example.

True Color Recovery and False-color Vessel Contrast Enhancement

True color image shows the natural color of the subject as it appears to human eyes. True color is an important information of retinal photographs which helps ophthalmologists to evaluate eye diseases such as age-related macular degeneration. The true color retinal image reconstructed from spectra can include an overall yellowish color due to the restricted illumination wavelength range. The arteries are light red and the veins are dark red, which is consistent with common color fundus images.

The representative reflection spectra of artery, vein and surrounding retinal area can be shown in the image(s). Artery and vein show different spectral signatures due to the different $sO_2$ levels. The spectra signatures are closer to the convoluted hemoglobin absorption spectra rather than the original spectra due to the limited spectral resolution of SRDA. Surrounding retinal area has a relatively flat spectrum. Small spectral variation in surrounding area may due to the nerve fiber scattering or the unresolved small vessels.

Vessel contrast enhancement is a useful procedure in vascular visualization and segmentation. We utilized the spectral information from hyperspectral retinal image and composed a false-color image with enhanced vessel-tissue color contrast. In the false-color coding, we empirically selected the 598 nm image channel minus 474 nm channel as blue channel, 549 nm minus 474 nm as green channel and 474 nm image as red channel, for example. This arrangement aims to maximize the contrast difference between blood and tissue, and adjust the appearance of vessels in red and tissue in white. The false color retinal image (e.g., FIG. 8C) can be compared with the true color image (e.g., FIG. 8A), and the false color clearly shows sharper retinal vessel color contrast. Some choroidal vessels hidden in our true color image are also visualized in the false color image.

In Vivo Retinal $sO_2$ Measurement

The results of in vivo retinal sO2 measurement can also be demonstrated. We calculated the blood vessel OD spectra by the equation $-\log_{10}(I_{in}/I_{out})$, where $I_{in}$ and $I_{out}$ are the spectra of vessel and the area adjacent to the vessel respectively. OD spectrum was averaged for each vessel to minimize the spectral instability. $sO_2$ is calculated by least-square fitting OD spectra to Eq. 1 using attenuation spectra. FIG. 9A, for example, shows the $sO_2$ map overlapped with the retinal image. The corresponding $sO_2$ values for individual vessels are shown in FIG. 9B. Arteries and veins show very distinct $sO_2$ values as artery $sO_2$ values are averagely higher than vein's by 0.3, for example. However, the absolute values are lower than other retinal oximetry reports, where arteries $sO_2$ values should be close to 1 and vein $sO_2$ values should be around 0.6 to 0.7, for example.

Several factors could cause bias of $sO_2$, including inhomogeneous reflection from selected reference, melanin concentration in the retinal pigment epithelium (RPE) and multiple light scattering. One important assumption for selection of reference $I_{out}$ in OD calculation is that the reflectivity from retina beneath the vessel is the same as from adjacent area. That assumption may not be the case due to the non-uniform distribution of retinal capillaries and choroidal vessels and melanin in RPE. Melanin has wavelength-dependent optical scattering and absorption coefficients, possibly causing errors in vessel OD extraction. Multiply light scattering may blend different light path together, e.g., light path passing vessel twice, passing once or even reflected by vessel upper surface, and cause unpredictable spectral variations. With all those factors together, estimated vessel OD could deviate from the real value and cause bias in sO2 calculation. The inaccuracy of $sO_2$ estimation from retinal imaging is reported elsewhere and is numerically analyzed by Mont Carlo method, for example.

Discussion

The SRDA hyperspectral imaging solution meets the compactness requirement of commercial ophthalmological instruments. The regular-sized detector can be simply installed on standard camera ports. The pre-calibration and post data processing are simple and straightforward. Compared with most other scanning/snapshot technologies requiring filter scanning or equipping dispersive components, SRDA dramatically simplified the imaging system. Such a scheme also enables low cost, portable hyperspectral imaging devices for other medical imaging applications, which is suitable for rural health clinics and point-of-care disease diagnosis. Furthermore, the dielectric film fabrication is fully compatible with CMOS fabrication process. Monolithically fabricated FP filters are capable of being integrated into current consumer imaging products, such as web camera and cellphone camera, making it possible to bring hyperspectral imaging functionality into remote diagnostics.

SRDA is very suitable for time-resolved hyperspectral monitoring. The frame rate is only limited by detector arrays and detector sensitivities. Without compromising imaging quality, we have demonstrated 20 fps imaging speed, which is about 4 times higher than the previous reports, for example. The maximum frame rate of this SRDA is 340 fps, for example. Such a high frame rate may also provide an opportunity to study transient spectral changes in retinal neural reactions to light. Other potentially applicable time-resolved functional imaging applications includes real-time Raman microscopy, fluorescence imaging and optical backscattering spectroscopic imaging.

The current SRDA has its own limit on spectral resolution and wavelength range. The SRDA provides 16 wavelength channels, 10 to 15 nm spectral resolution in a wavelength range of 160 nm. It is worse than the disperser based hyperspectral imaging of 48 channels with 4 to 10 nm resolution in 200 nm range, for example. The channel number of SRDA is currently limited by the number of camera sensing elements. Increasing wavelength channels will bin more sensing elements to on hyperspectral imaging pixel and inevitably reduce the imaging spatial resolution. Fortunately, commercial cameras with pixel numbers from 10 to 20 million, 5 to 10 times of our current sensing chip, for example, have become the main stream in the market. By employing such cameras, 80 to 160 channels can be realized under our current pixel number, for example. The spectral resolution and wavelength range are ultimately limited by the transmission bandwidth of each channel and the FP cavity second transmission band. Those limits are highly related to the FP design and fabrication. Multiple dielectric layer (MDL) can effectively reflect light from visible to NIR range. MDL cavities support strong light confinement and theoretically can achieve sub-nanometer transmission. We believe employing MDL cavities in the future will fundamentally increase the spectral resolution and wavelength range of SRDA, making SRDA a very competitive candidate over other hyperspectral imaging technologies.

Conclusion

In conclusion, we utilized a novel SRDA and built a compact, high-speed hyperspectral fundus camera for rats. We successfully acquired "true-color" retinal images on rat in 16 bands from 470 to 630 nm in video rate, for example. We also demonstrated false-color vessel contrast enhancement and retinal $sO_2$ measurement through spectral analysis. This work demonstrated a hyperspectral imaging strategy compatible with most ophthalmoscopic instruments and brought the hyperspectral retinal imaging closer to the final clinical uses. This strategy also provides an alternative in other time-resolved hyperspectral imaging applications.

Example 2

Hyperspectral retinal imaging is a novel technique that can non-invasively capture spatially-resolved spectral information from the retina. Conventional fundus imaging detects either monochromatic or full-spectrum light that is reflected by retinal structures, providing great spatial detail of the retina I(x,y). Hyperspectral imaging adds the ability to quantify the spectra of the light reflected by the retina in the same spatial detail I(x,y,λ). As different structures and chemicals have unique spectral reflectance properties, hyperspectral imaging provides another dimension of information for researchers studying human tissue. In the last decade, spectrally-based measurements of retinal vessel oxygenation have allowed for the study of tissue perfusion and metabolic demands of the retina. Similarly, spectral reflectance signatures are being used to help localize molecules and cell types within the retina.

As the use of hyperspectral imaging is evolving and expanding in ophthalmology, so too are the systems themselves. Early hyperspectral systems collected spectral information in an image by scanning through either wavelength (λ) or position (x,y) in the image plane. These scanning-type systems required minutes to acquire a complete dataset and relied on complicated image rectification that is prohibitive when imaging a non-fixed object like the eye. More modern hyperspectral systems have combined high resolution detectors with more sophisticated optics to allow for simultaneous imaging in multiple wavelengths. Without lag or scanning time, newer snapshot systems collect an information-dense hyperspectral data cube I(x,y,λ) in a single image. The collection time is limited only by the exposure time of the camera, and thus, does not require image rectification or extensive post-processing to limit motion artifacts.

One example snapshot hyperspectral imaging system is a compact, versatile tool that allows for quick, non-invasive spectral study of the retina without moving parts, imaging lag, or complicated optical components. The IMEC high speed imaging (HIS) camera is a system based on a mosaic layout of Fabry-Perot filters atop a CMOS detector, for example. With 16 bands from 458 nm to 587 nm and 256×512 pixels of resolution, for example, we can capture rich hyperspectral datacubes with the ease and flexibility of a normal CMOS camera. One of the largest benefits is that the IMEC camera design does not require any additional optical image splitting or complicated filters. This allows for simple integration to a standard fundus camera for fundus imaging.

Certain examples demonstrate the versatile and robust data collection capabilities our hyperspectral retinal imaging system by performing spectra-based retinal oximetry measurements on 10 healthy patients.

Principles of Retinal Oximetry

A dual wavelength algorithm for computing retinal vessel oximetry from reflectance measurements was detailed by Hickam in 1963. In this algorithm, the optical density can be derived from the ratio of light absorption at and near the vessel. The ratio of optical densities at the isobestic wavelength and a second wavelength, which favors absorption by oxy hemoglobin only, is proportional to the oxygen saturation of the blood in the vessel. Attempts to improve this method have included 3 wavelength techniques with vessel tracking as well as the use of optical filters and elements to create identical images simultaneously in multiple wavelengths. Several popular current commercial retinal oximetry devices are based on a derivative of this 2 wavelength approach (Oxymap, Imedos), while newer hyperspectral systems have demonstrated the ability to use of the entire absorbance spectra of hemoglobin in determining the oxygen saturation.

Our snapshot system captures reflected light across 16 wavelengths, for example. To analyze oxygen saturation, we utilize the entirety of the collected spectra with a least-squares fit to determine the quantity of oxygenated hemoglobin in retinal vessels.

Methods

System

Figure 12:
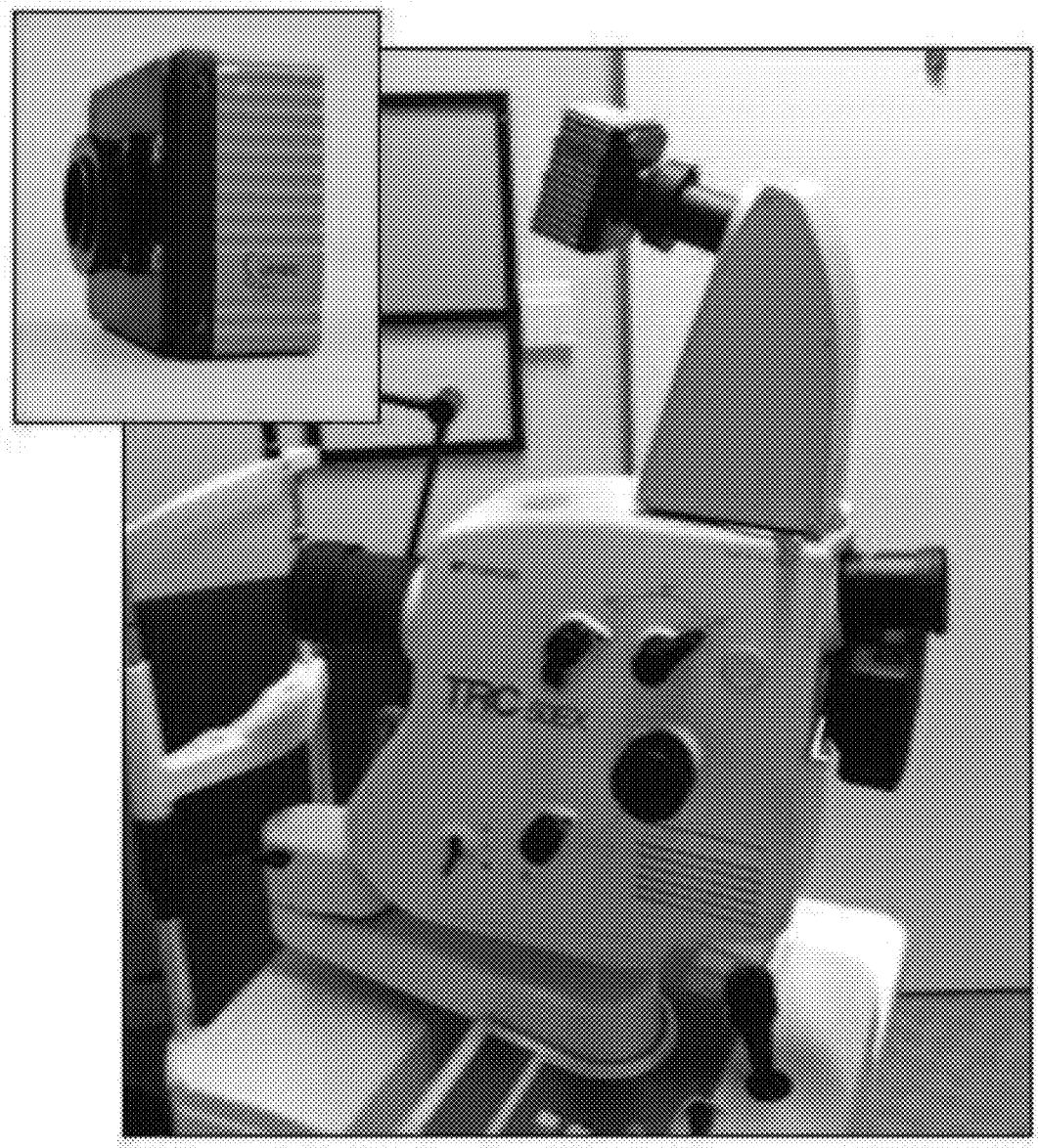
FIG. 12 illustrates an example high speed imaging camera integrated onto a fundus camera.

An example integrated HSI/fundus camera system is shown in FIG. 12. In FIG. 12, an HSI camera (e.g., IMEC HIS camera, etc.) is integrated onto a fundus camera.

The core of the system in this illustrated example is the IMEC hyperspectral imaging detector. The detector includes a mosaic pattern of 16 different Fabry-Perot narrow-band spectral filters, with emissions ranging from 458 nm to 587 nm, manufactured directly onto a 1024×2048 pixel CMOSIS CMV2000 CMOS imaging sensor, for example. The filters are arranged in a 4×4 mosaic pattern, with each filter covering a single pixel, for example. The mosaic pattern of filters is repeated across the CMOS sensor, resulting in an effective spatial resolution of 256×512 pixels in each of the 16 bands, for example. The detector is housed in an ADIMEC quartz series camera body measuring 80 mm square and weighing just 400 g, for example. To prevent contamination from light outside the spectral range of the detector, a band-pass filter set was installed in the lens mount of the camera to pass light between 450 nm and 600 nm, for example.

The detector and filter set were installed on a commercial fundus camera with an off-the-shelf relay lens system. By experiment, we found that the 35° FOV setting on the fundus camera provided adequate visualization of the vessels surrounding the optic disc with a sufficiently broad depth of focus. The camera's electronic shutter was operated via its Camera Link data port by a PC running framegrabber software supplied by IMEC. In order to calibrate the system, a monochromator was used to measure the response of each channel in increments. The resulting response curves were used to adjust for differences in throughput amongst the 16 channels (see, e.g., FIG. 13).

Subjects

To demonstrate the performance capabilities of the system, we recruited 11 healthy volunteers with no known ocular disease for fundus imaging with the HSI system. The mean age of the group was 48.0+/−20.3, range 21 to 80 with 6 males and 5 females. Volunteers were dilated with a combination of Tropicamide 1% (and) Phenylephrine Hydrochloride (2.5%) drops. For each subject, images were taken of the optic disc at 35° FOV with the HSI system.

This study was approved by the institutional review board of Northwestern University (STU00063366-MOD0003) and adhered to the tenets of the Declaration of Helsinki for research involving human subjects. Each participant gave informed consent after explanation of the nature and possible consequences of the study.

Retinal Oximetry

From the collected hyperspectral fundus images, the vessel A-V difference was measured using a multi-wavelength curve fitting analysis, as shown in FIGS. 14A-14D.

Figure 14A:
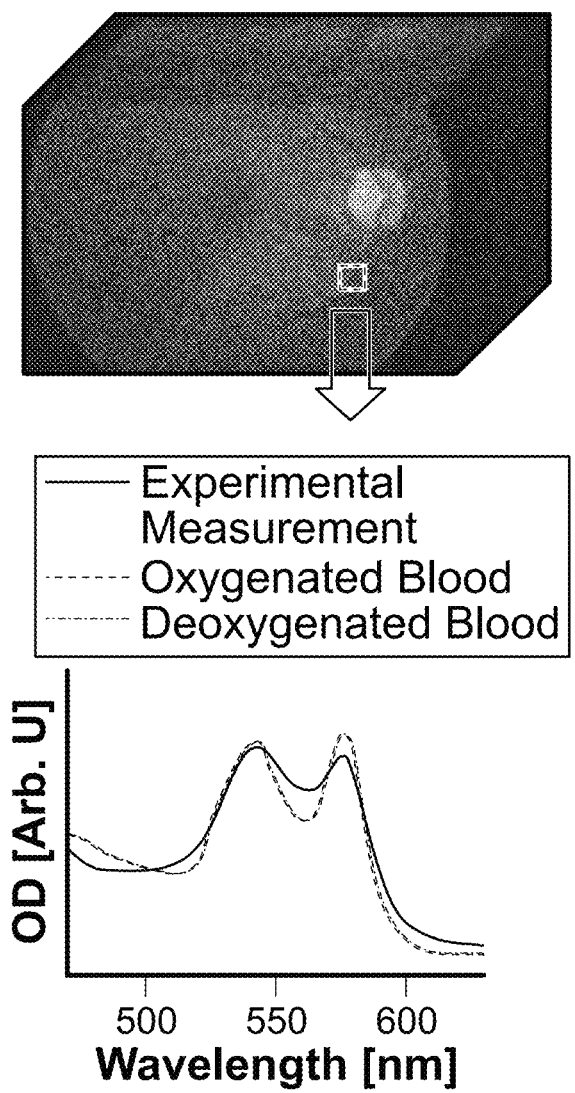

FIGS. 14A-14D depict an example calculation of a vessel. FIG. 14A shows vessels near the optic disc are selected, and the spectra is analyzed to determine the content of oxygenation and deoxygenated blood. As shown in FIG. 14B, the results are mapped onto an image of the vessels to visualize gradients. As illustrated in FIG. 14C, a chart representation of the data highlights the difference between artery and vein. In the example of FIG. 14D, the average A-V difference is plotted.

In addition to comparing data from volunteers, the repeatability of the system was assessed by imaging the same eye 6 times within one session, minimizing the time between images (e.g., <30 seconds). With the subject at steady-state, the goal is to determine the variability introduced purely by the system.

Results

Figure 15:
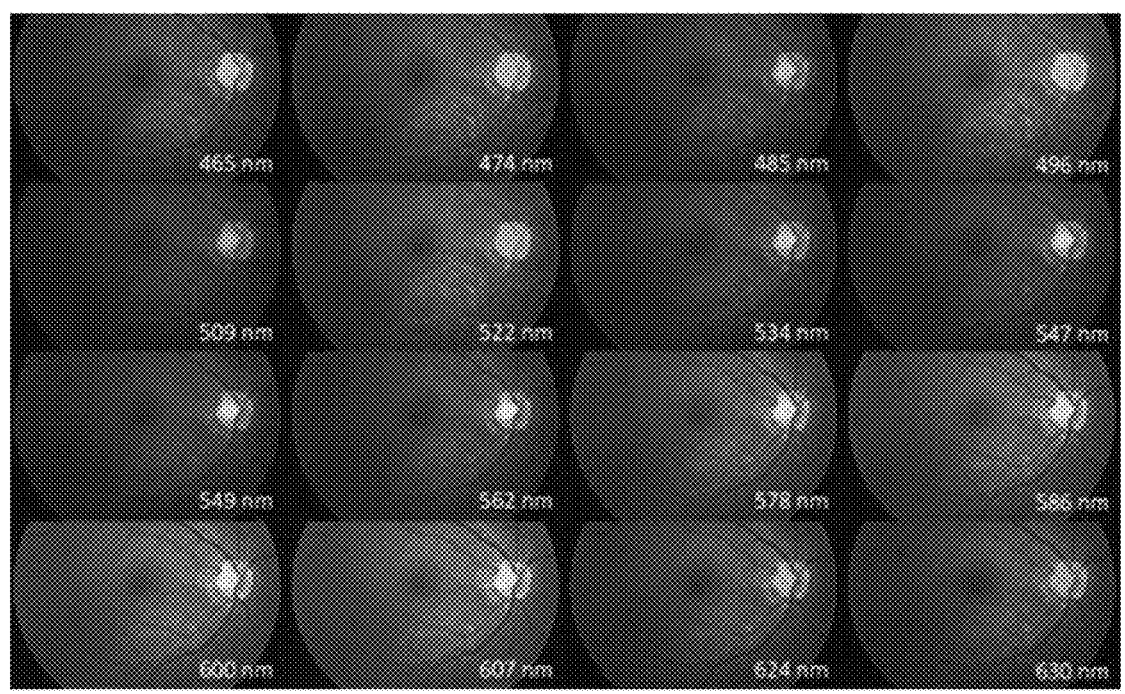
FIG. 15 illustrates a visualization of an example hyperspectral datacube with false coloring applied to emphasize different channels.

An example visualization of the hyperspectral datacube output is shown in FIG. 15. Spectral analysis of the fundus images enhances visualization of distinct features in the retina. For example, vessel detail is best seen in wavelengths greater than 550 nm where absorption from hemoglobin causes the vessels to appear dark. FIG. 15 shows a visualization of hyperspectral datacube with false coloring applied to emphasize the different channels.

The results of the vessel oxygenation analysis are shown in Table 1. The mean A-V difference varied between 0.205 and 0.319, while the standard deviation of that mean was between 0.039 and 0.197, for example.

TABLE 1

Subject data and results

| Patient ID | Sex | age | Arteries | | Veins | | A-V difference | |
|---|---|---|---|---|---|---|---|---|
| | | | mean | std | mean | std | mean | std |
| WZL | M | | 0.921 | 0.050 | 0.620 | 0.032 | 0.301 | 0.060 |
| Joel* | M | 29 | 0.930 | 0.032 | 0.611 | 0.022 | 0.319 | 0.039 |
| P21test4* | M | 24 | 0.893 | 0.080 | 0.644 | 0.075 | 0.250 | 0.109 |
| control1 | F | 31 | 0.899 | 0.132 | 0.588 | 0.143 | 0.311 | 0.195 |
| p069 | F | 21 | 0.920 | 0.129 | 0.649 | 0.149 | 0.271 | 0.197 |
| p70 | M | 59 | 0.852 | 0.066 | 0.612 | 0.050 | 0.240 | 0.083 |
| p76* | F | 55 | 0.926 | 0.143 | 0.629 | 0.110 | 0.298 | 0.180 |
| p80test3 | M | 27 | 0.913 | 0.060 | 0.708 | 0.059 | 0.205 | 0.084 |
| p81+ | F | 74 | 0.954 | 0.097 | 0.700 | 0.077 | 0.254 | 0.124 |
| p83 | M | 61 | 0.914 | 0.080 | 0.647 | 0.082 | 0.267 | 0.114 |
| p84* | M | 50 | 0.912 | 0.082 | 0.675 | 0.060 | 0.236 | 0.102 |

To assess the repeatability of the system, the results of 6 consecutive images of the same eye were compared. The standard deviation of O2 sat measurements was 0.014, for example.

Discussion

In summary, we demonstrate a snapshot hyperspectral system capable of taking high-quality spectral images in-vivo. To our knowledge, this is the first mosaic type snapshot hyperspectral detector demonstrated in this capacity. This system is compact, easily integrated, and straightforward to operate. The mosaic filter design provides good spectral and spatial resolution without the need for complicated post-processing or image reconstruction.

We've demonstrated the clinical utility of the system by performing retinal oximetry measurements on a series of healthy subjects. The data from our small cohort agrees with other published retinal oximetry data. The variation in this measurement between subjects could be due to physiologic difference in retinal O2 consumption, subclinical pathology (small vessel disease) or differences in vitreous media opacity. Regardless, we feel these results prove that the system is capable of performing in-vivo studies with reliable performance and easy operation. Additionally, the data reveals excellent intra-subject variability (e.g., std=0.014) across the entire fundus, demonstrating excellent repeatability.

As demonstrated in FIG. 15, spectral decomposition of retinal reflectance helps to highlight specific structures in the retina. In addition to oximetry measurements, spectral analysis of fundus photography has been shown to yield information about location of macular pigment. We feel that the high resolution spectral-spatial data provided by this system has the potential to allow for detection, localization, and even identification of retina components and pathological elements.

Figure 13:
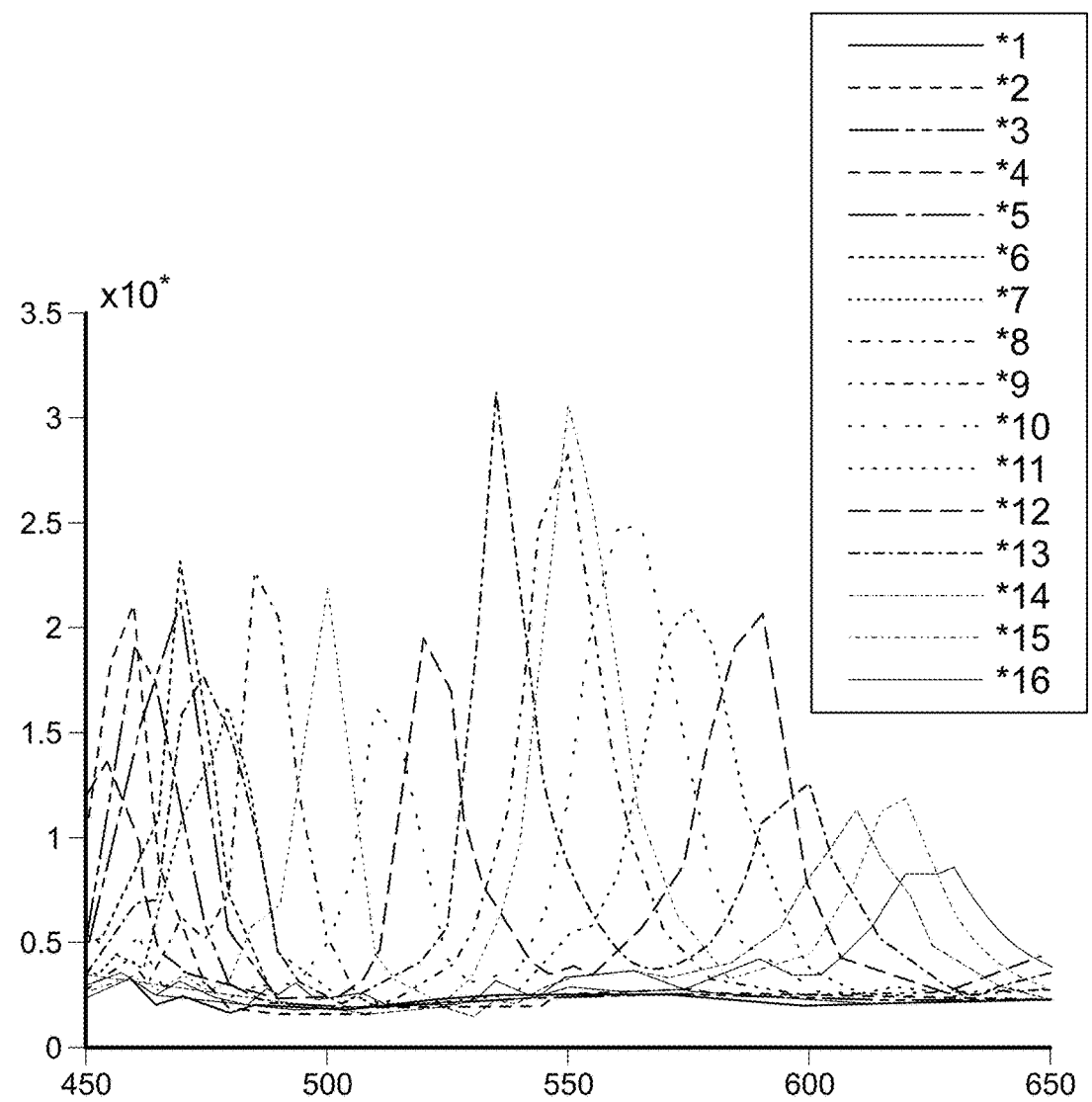
FIG. 13 depicts example response curves for each of 16 channels of an example detector.

A drawback to the system is that several channels have significant second-order effects (as seen in the example of FIG. 13). In many cases, the second-order contributions of the filters were up to 50% of the intensity of the primary response, making pure spectral decomposition a challenge. In our analysis, we were able to anticipate these effects by convoluting. The detector manufacturer claims that future design iterations of this detector will significantly minimize second-order effects, resulting in a more simple spectral recovery.

An additional downside of this system is the limited spectral range of the detector. While the 458-587 nm spectral range, for example, is well suited for oximetry measurements, it is lacking reception near the UV and IR boundaries of the visible spectra. To reduce second-order effects, a bandpass filter is used to exclude light <450 nm and >600 nm, for example. Consequently, color recovery from the detector is missing red and blue tones, causing the "pseudo-color" reconstruction to look abnormal. An expanded spectral range will allow for better color approximation of the data and may help to visualize additional components that interact outside the current spectral range of our detector.

Visible Light OCT Endoscopy Example Systems and Methods

OCT and related techniques, such as described above, can also be used with visible light OCT (vis-OCT) for endoscopy and disease detection.

Colposcopy is the current standard imaging device for cervix/vagina diseases detection, and for treatment monitoring. However, with limited sensitivity, colposcopy can only detect the presence of significant changes on the surface epithelium of cervix/vagina, such as focal bleeding, ulcers, peeling, and vasculature changes. Recent study suggested that sub-epithelial structural changes may be involved in cervix/vagina complications. Thus, an imaging device with high depth resolution and big penetration depth is highly desired for advanced cervix/vagina diseases detection. Using wideband illumination and interferometric sensing, optical coherence tomography (OCT) can achieve micrometer level axial resolution imaging with millimeter-level penetration depth. In this view, OCT has great potential applications for cervix/vagina imaging. Previous research demonstrated that OCT with near infrared light illumination (1310-nm central wavelength, for example) that is able to image two layers of vagina: the epithelium layer and the submucosa layer. Because of long central wavelength employed, the reported NIR-OCT endoscopy, however, provided a limited depth resolution (e.g., around 20 μm). Besides, according to the published results, the imaging contrasts between epithelium layer and the submucosa layer are not very distinctive using NIR illumination. Certain examples use a table top visible light OCT system (Vis-OCT) in which the epithelium layer and the submucosa layer can be clearly vascularized with distinctive contrast. Certain examples provide vis-OCT endoscopy for cervix/vagina imaging applications.

Visible Light Optical Coherence Tomography (Vis-OCT) Endoscopy System

Figure 16:
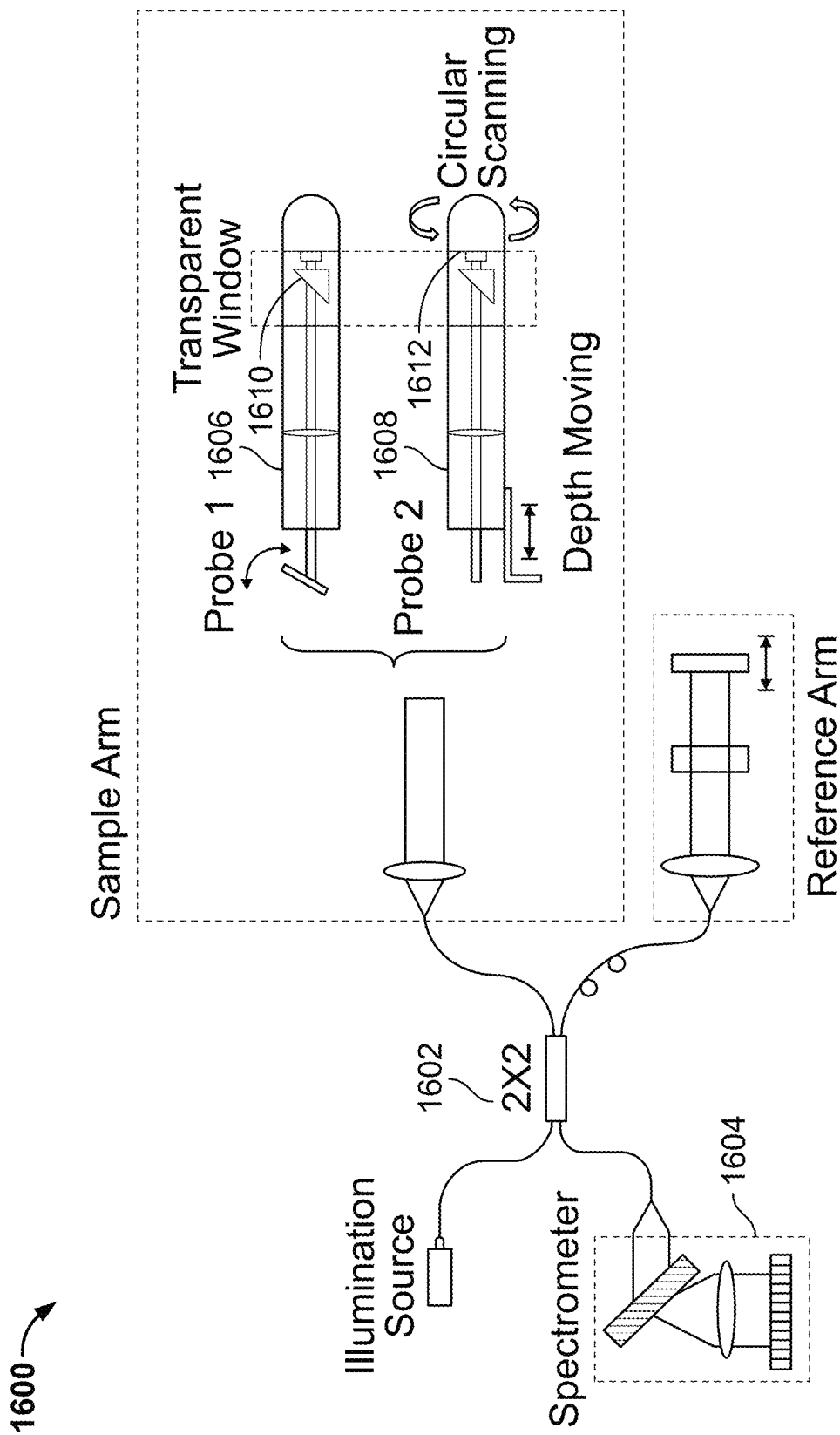
FIG. 16 illustrates an example fiber-based visible light OCT endoscopy system.

Certain examples provide a fiber based Vis-OCT endoscopy system 1600. The schematic is shown in FIG. 16. The example uses wide range visible light for illumination (e.g., from 520 nm to 610 nm), which enables high axial imaging resolution up to 1.5 µm in the air, for example. FIG. 16 employs a fiber coupler 1602 (e.g., with a split ratio 50/50) for interferometric signal sensing, and a spectrometer 1604 to detect and digitize interference signals. In an example, the spectrometer 1604 offers a 0.044-nm spectral resolution and a maximum A-line rate of 70 KHz. The axial imaging range of the current vis-OCT endoscopy is up to 1.7 mm, for example. For flexible imaging, two types of probes can be used, as shown in FIG. 16 (Probe 1 1606 and Probe 2 1608). Probe 1 is designed for targeted area screening (e.g., 5 mm by 5 mm imaging area, 512 A-lines by 512 A-lines or 256 A-lines by 256 A-lines, etc.), and is suitable for detailed examination of region of interest on vaginal wall. Galvo mirrors can be used to scan probe beam into the probe 1, and the scanning beam is further relayed to the imaging sample by a reflection mirror 1610 mounted at the tip part of probe 1. The collimated beam from OCT engine is focused into vaginal wall by an anti-reflection coated achromatic doublet lens with 70-mm focus length and 0.5-inch diameter, for example, mounted in probe 1. Probe 2 is designed for whole vagina screening. There is a motor 1612 built in probe 2, responsible for circularly scanning illumination beam onto the sample. There is another motor attaching to probe 2, which drives probe 2 to different depth locations in vagina, enabling to screen the whole vagina. During imaging, probe 1 and probe 2 can be interchanged. For example, an anti-reflection coated achromatic doublet lens with 35-mm focus length and 0.5-inch diameter, for example, can be used to focus the beam into vagina wall. The prototypes of probe 1 and probe 2 are shown in the example of FIG. 16, and an associated imaging speed is determined by spectrometer speed, which has as maximum A-line rate at 140 KHz, for example. In certain examples, we tested the sensitivity of the Vis-OCT endoscopy to be 90 dB under 1 mw laser illumination, and the roll of sensitivity is 15 dB.

Some Examples

Figure 17:
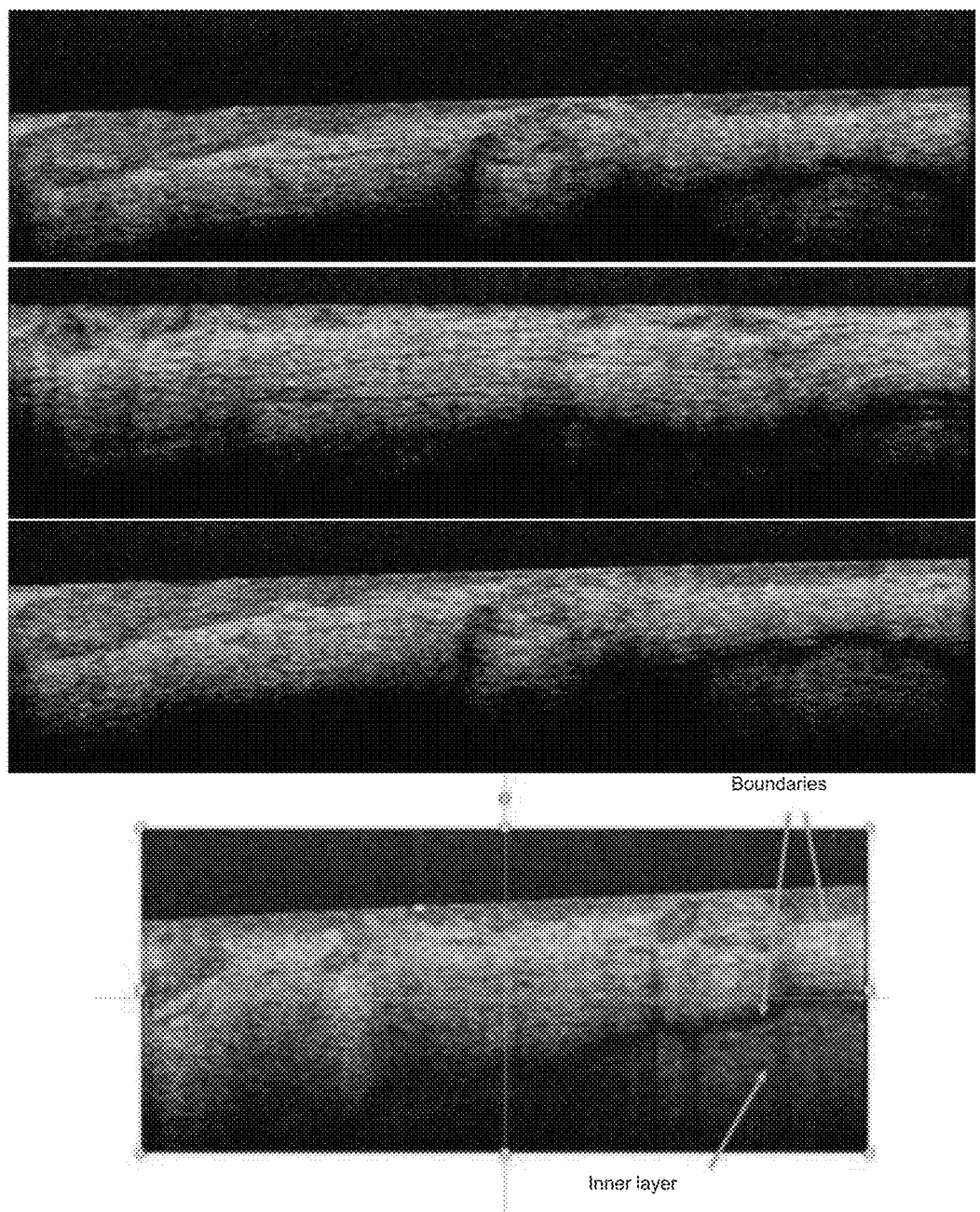

Example 1—As shown in FIG. 17, images were taken from an outer segment of FRT. Image quality was improved. Image range was 5 mm wide. Clear layer structures were observed in some of B-scan images.

Figure 18:
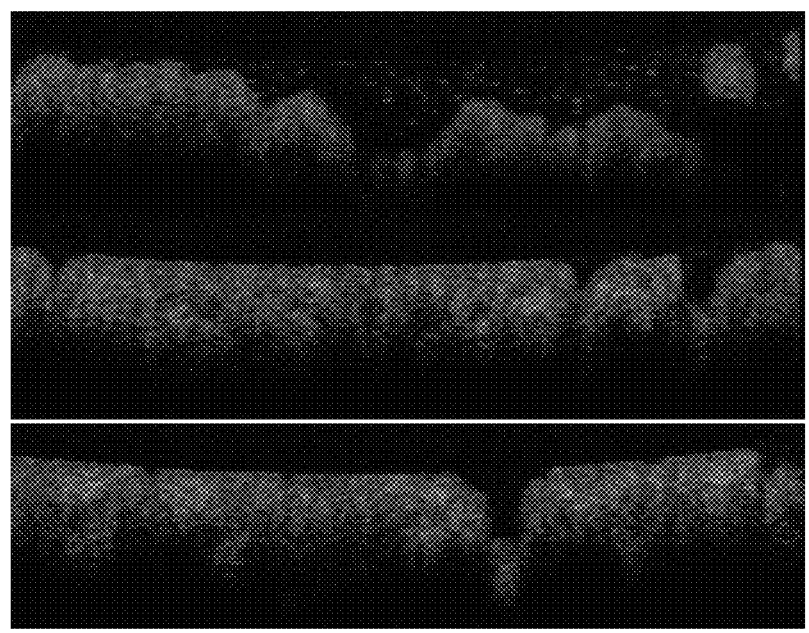

Example 2—As shown in FIG. 18, images were taken from an inner segment of FRT. Image quality was different (worse) from outer segment. Image range was 5 mm wide. Almost no layer structure was observed.

Figure 19:
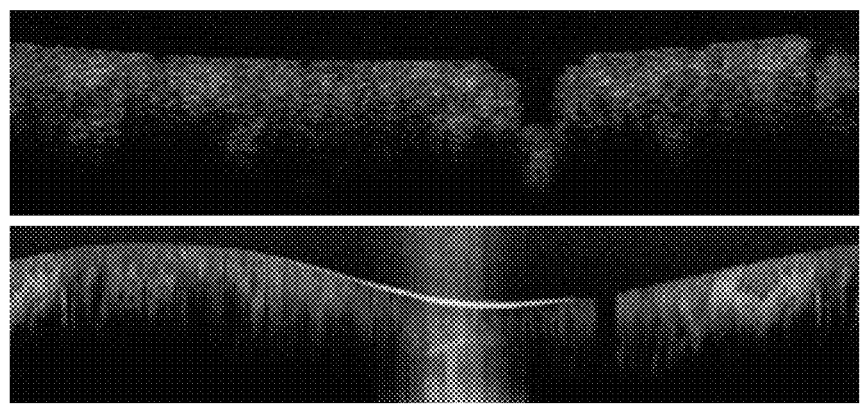

Example 3—As shown in FIG. 19, images were taken from an outer segment of FT using circular scanning. Layer structures are clearly observed in some areas.

Figure 20A:
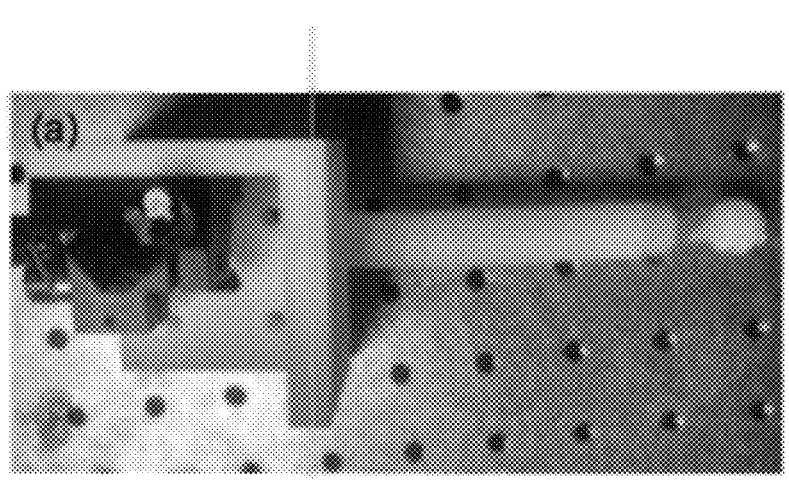
Figure 20B:
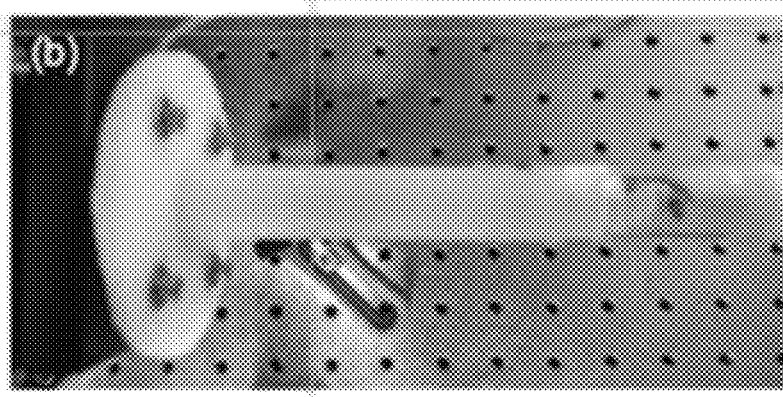
Figure 22:
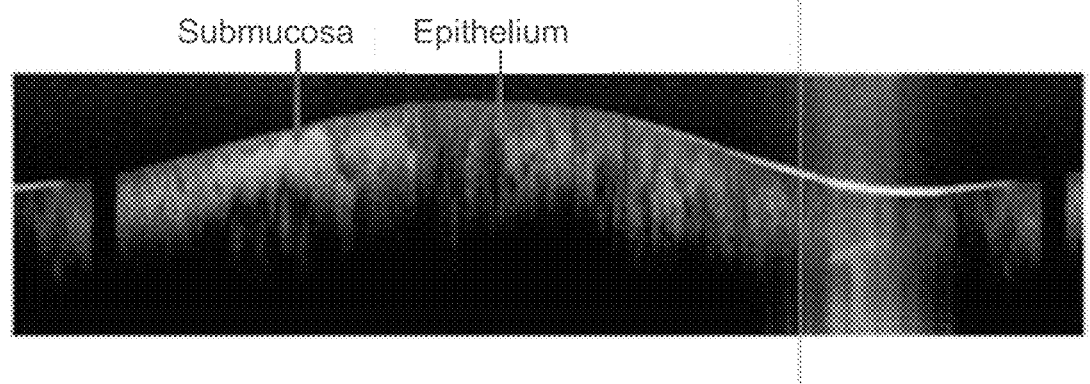

Example 4 shows first and second probes in FIGS. 20A-20B, and bscan vaginal images from probe 1 of FIG. 20A are shown in FIGS. 21A-21B, including indication of the epithelium and submucosa. FIG. 21C shows an enface image of 5 mm by 5 mm. FIG. 22 shows an example circular image of macaque vagina from probe 2 of FIG. 20B.

Figure 23:
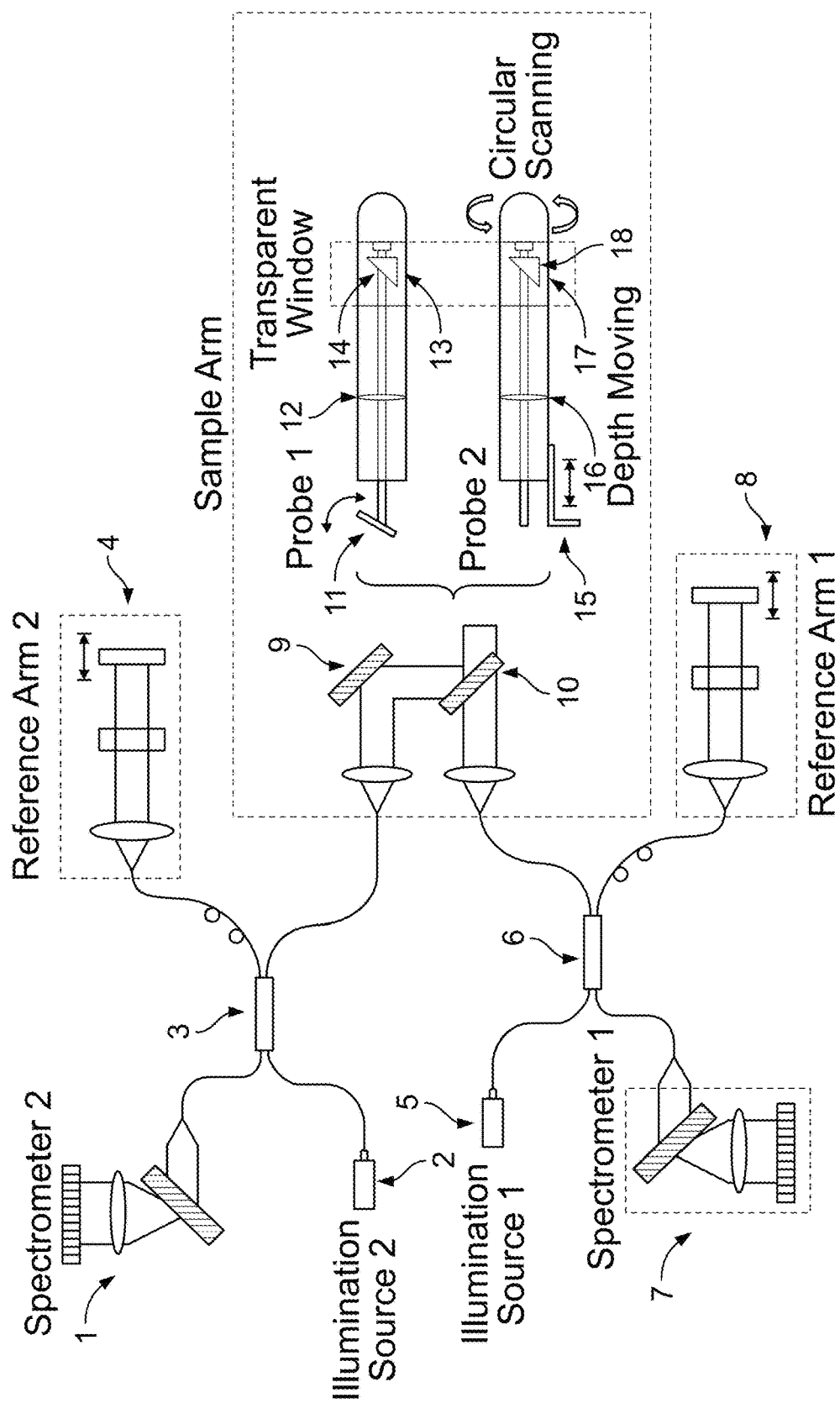
FIG. 23 shows a schematic of an example vs-OCT endoscopy system.

FIG. 23 shows a schematic of an example vs-OCT endoscopy system. As shown in the example of FIG. 23, a fiber-based Vis-OCT endoscopy system can include dual spectrometers 1, 7 with dual illumination sources 2, 5 in conjunction with a pair of fiber couplers 3, 6. As shown in the example of FIG. 23, reference arms 4, 8 are coupled to the spectrometers 1, 7 and illumination sources 2, 5, and a sample arm via the fiber couplers 3, 6. The sample arm includes first and second probes, in which probe 1 is designed for targeted area screening and is suitable for detailed examination of a region of interest (e.g., on a vaginal wall, etc.) via mirror 11, lens 12 and a transparent window 13, 14. Probe 2 is designed for whole area (e.g., whole vagina, etc.) screening. A motor 17, 18 in probe 2 allows a scanning illumination beam to be circularly focused onto a target or sample via a lens 16. The probe 2 can also be adjustable (e.g., depth moving 15). As shown in the example of FIG. 23, a series of mirrors 9, 10 is used to scan a beam into the probes 1 and 2.

Example Software and Computer Systems

In various examples, methods and systems described and disclosed herein may further include software programs on computer systems and use thereof. Accordingly, computerized control for the synchronization of system functions such as laser system operation, fluid control function, and/or data acquisition steps are within the bounds of the present disclosure. The computer systems may be programmed to control the timing and coordination of delivery of sample to a detection system, and to control mechanisms for diverting selected samples into a different flow path. In some examples of the invention, the computer may also be programmed to store the data received from a detection system and/or process the data for subsequent analysis and display.

Figure 24:
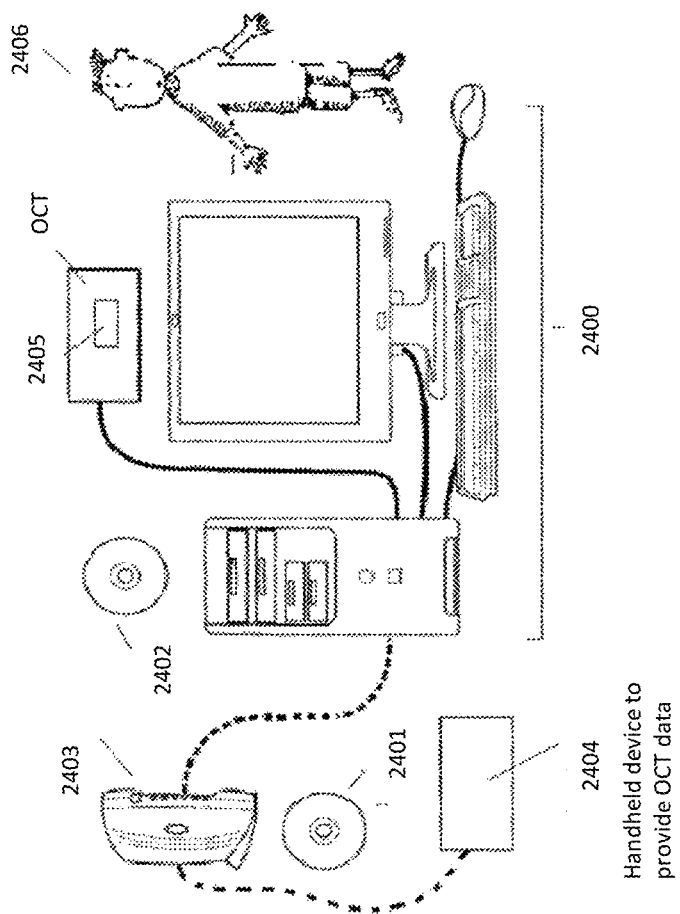
FIGS. 24-26 illustrate example computer systems that can be used to implement the systems, apparatus, and methods described and disclosed herein.

The computer system 2400 illustrated in FIG. 24 may be understood as a logical apparatus that can read instructions from media 2401, 2402 and/or a network port, which can optionally be connected to server 2403 having fixed media 2401, 2402. The system, such as shown in FIG. 24 can include a CPU, disk drives, optional input devices such as handheld devices for acquiring OCT objective focal length free flow measurement data 2404 or other instrument types such as a laboratory or hospital based instrument 2405. Data communication can be achieved through the indicated communication medium to a server at a local or a remote location. The communication medium can include any device for transmitting and/or receiving data. For example, the communication medium can be a network connection, a wireless connection or an internet connection. Such a connection can provide for communication over the World Wide Web and/or a private network, etc. It is envisioned that data relating to the present disclosure can be transmitted over such networks or connections for reception and/or review by a party 2406 as illustrated in FIG. 24.

Figure 25:
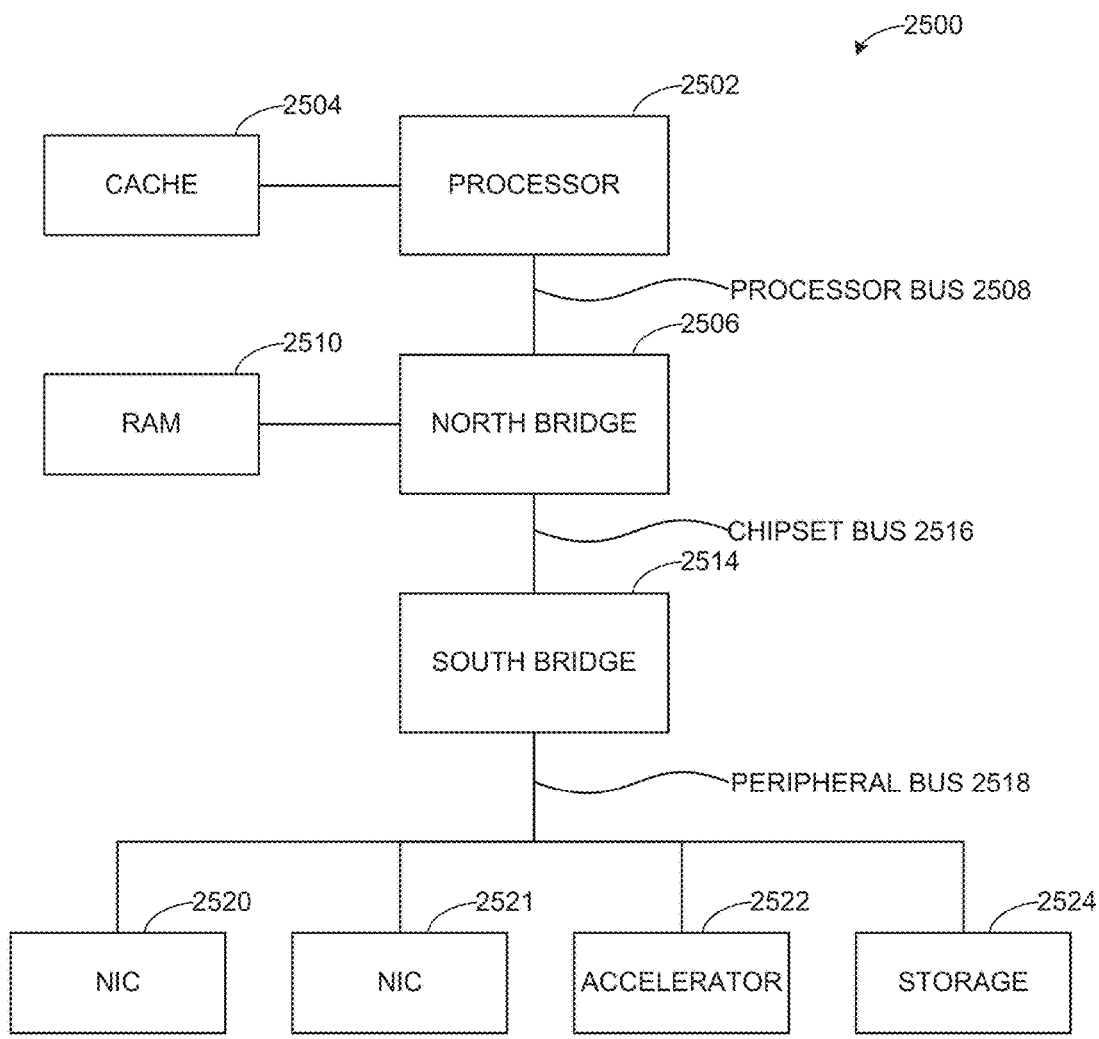

FIG. 2500 is a block diagram illustrating a first example architecture of a computer system 2500 that can be used in connection with examples disclosed and described herein. As depicted in FIG. 25, the example computer system can include a processor 2502 for processing instructions. Non-limiting examples of processors include: Intel Xeon™ processor, AMD Opteron™ processor, Samsung 32-bit RISC ARM 1176JZ(F)-S vl.O™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some examples, multiple processors or processors with multiple cores can also be used, whether in a single computer system, in a cluster, or distributed across systems over a network comprising a plurality of computers, cell phones, and/or personal data assistant devices.

As illustrated in FIG. 25, a high speed cache 2504 can be connected to, or incorporated in, the processor 2502 to provide a high speed memory for instructions or data that have been recently, or are frequently, used by processor 2502. The processor 2502 is connected to a north bridge 2506 by a processor bus 2508. The north bridge 2506 is connected to random access memory (RAM) 2510 by a memory bus 2512 and manages access to the RAM 2510 by the processor 2502. The north bridge 2506 is also connected to a south bridge 2514 by a chipset bus 2516. The south bridge 2514 is, in turn, connected to a peripheral bus 2518.

The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 2518. In some alternative architectures, the functionality of the north bridge can be incorporated into the processor instead of using a separate north bridge chip.

In some examples, system 2500 can include an accelerator card 2522 attached to the peripheral bus 2518. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 2524 and can be loaded into RAM 2510 and/or cache 2504 for use by the processor. The system 2500 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with certain examples.

In this example, system 2500 also includes network interface cards (NICs) 2520 and 2521 connected to the peripheral bus for providing network interfaces to external storage, such as Network Attached Storage (NAS) and other computer systems that can be used for distributed parallel processing.

Figure 26:
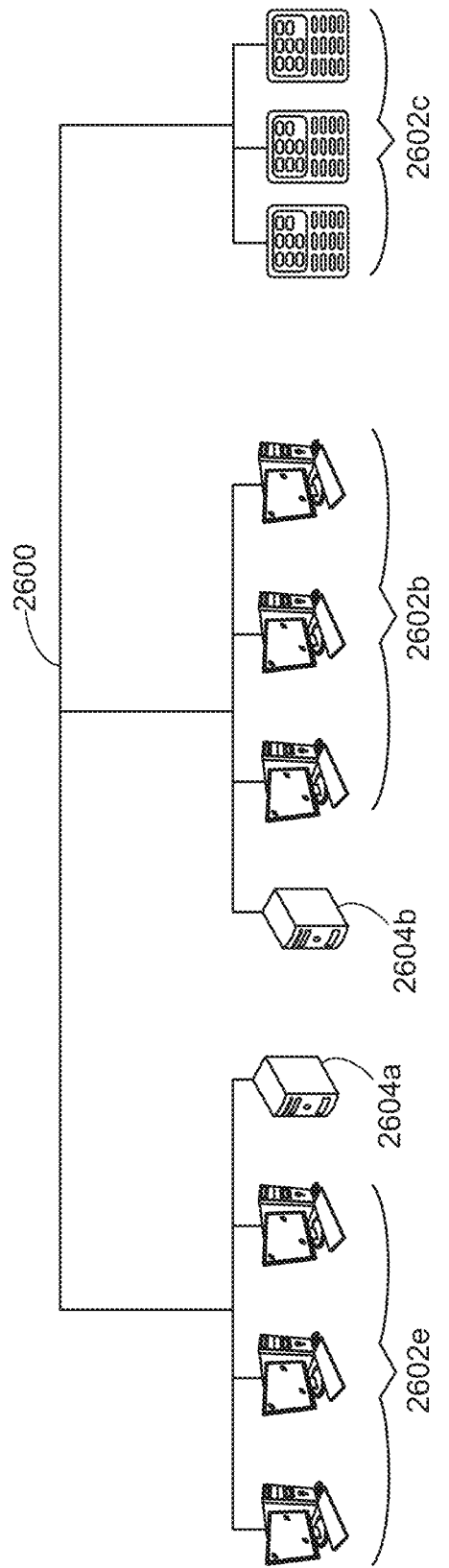

FIG. 26 is a diagram showing a network 2600 with a plurality of computer systems 2602a, and 2602b, a plurality of cell phones and personal data assistants 2602c, and Network Attached Storage (NAS) 2604a, and 2604b. In some examples, systems 2602a, 2602b, and 2602e can manage data storage and optimize data access for data stored in Network Attached Storage (NAS) 2604a and 2604b. A mathematical model can be used for the data and be evaluated using distributed parallel processing across computer systems 2602a, and 2602b, and cell phone and personal data assistant systems 2602c. Computer systems 2602a, and 2602b, and cell phone and personal data assistant systems 2602c can also provide parallel processing for adaptive data restructuring of the data stored in Network Attached Storage (NAS) 2604a and 2604b. FIG. 26 illustrates an example only, and a wide variety of other computer architectures and systems can be used in conjunction with the various examples of the present invention. For example, a blade server can be used to provide parallel processing. Processor blades can be connected through a back plane to provide parallel processing. Storage can also be connected to the back plane or as Network Attached Storage (NAS) through a separate network interface.

In some example examples, processors can maintain separate memory spaces and transmit data through network interfaces, back plane or other connectors for parallel processing by other processors. In other examples, some or all of the processors can use a shared virtual address memory space.

The above computer architectures and systems are examples only, and a wide variety of other computer, cell phone, and personal data assistant architectures and systems can be used in connection with example examples, including systems using any combination of general processors, co-processors, FPGAs and other programmable logic devices, system on chips (SOCs), application specific integrated circuits (ASICs), and other processing and logic elements. In some examples, all or part of the computer system can be implemented in software or hardware. Any variety of data storage media can be used in connection with example examples, including random access memory, hard drives, flash memory, tape drives, disk arrays, Network Attached Storage (NAS) and other local or distributed data storage devices and systems.

In some examples of present disclosure, the computer system can be implemented using software modules executing on any of the above or other computer architectures and systems. In other examples, the functions of the system can be implemented partially or completely in firmware, programmable logic devices such as field programmable gate arrays, system on chips (SOCs), application specific integrated circuits (ASICs), or other processing and logic elements.

What is claimed is:

1. A method for imaging a target, the method comprising:
   a. performing optical coherence tomography (OCT) scanning on the target with one or more beams of low coherence light, wherein the one or more beams of light comprise one or more near-infrared (NIR) wavelengths;
   b. acquiring interference signals generated by OCT scanning to determine a flow rate of a fluid in the target and generating a three dimensional (3D) image of the target;
   c. performing angiography on the target with fast scanning using narrow band illumination, wherein fast scanning corresponds to a frame rate of at least 40 Hz;
   d. acquiring optical attenuation spectra from the angiography at multi-wavelengths;
   e. determining a concentration of one or more analytes including oxygen saturation, from the acquired optical attenuation spectra from the angiography;
   f. determining a rate of change of the one or more analyte concentrations in the target based on the determining of flow rate of the fluid and a concentration of one or more analytes; and
   g. simultaneously quantitatively imaging the flow rate of the fluid in the target and the concentration of one or more analytes in the fluid in the target.

2. The method of claim 1, wherein the generating the 3D-imaging in the target is performed without contacting at least one analyte with an exogenous reagent or label.

3. The method of claim 1, wherein the OCT scanning generates one or more A-scans.

4. The method of claim 1, wherein angiography requires generating multiple repeated images, and calculation of differences or standard deviation among the acquired image sequence stacks at each illumination.

5. The method of claim 1, wherein angiography is performed with multiple wavelengths to collect optical attenuation spectra.

6. The method of claim 1, wherein the one or more beams of light are used to perform multi-beam or multi-band scanning OCT.

7. The method of claim 1 for angiography, wherein the one or more beams of light illuminate the target concurrently or sequentially.

8. The method of claim 1, wherein the OCT scanning on the target is performed with identical or different pre-defined scanning trajectories.

9. The method of claim 1, wherein the angiography on the target is performed with identical or different predetermined illumination wavelengths, bandwidth, illumination intensities.

10. The method of claim 1, wherein the angiography on the target is performed with identical or different predetermined repetition times and imaging field of views.

11. The method of claim 1, wherein the target is selected from the group consisting of tissue, healthy tissue, diseased tissue, retina, tumor, cancer, growth, fibroid, lesion, skin, mucosal lining, organ, graft, blood supply and one or more blood vessels.

12. The method of claim 1, wherein the quantitatively imaging the flow rate of the fluid in the target is performed using invisible light.

13. The method of claim 1, wherein the quantitatively imaging a concentration of one or more analytes, including oxygen saturation, in the fluid in the target is performed using visible light at multi-wavelengths.

14. The method of claim 1, wherein the fluid is selected from the group consisting of whole blood, blood plasma, blood serum, urine, semen, tears, sweat, saliva, lymph fluid, pleural effusion, peritoneal fluid, meningal fluid, amniotic fluid, glandular fluid, spinal fluid, conjunctival fluid, vitreous, aqueous, vaginal fluid, bile, mucus, sputum and cerebrospinal fluid.

15. The method of claim 1, wherein the analyte is selected from the group consisting of oxygen, hemoglobin, oxygenated hemoglobin, deoxygenated hemoglobin, glucose, sugar, blood area nitrogen, lactate, hematocrit, biomarker and nucleic acid.

16. The method of claim 1, wherein determining the rate of change of one or more analytes is performed by comparing or using a reference.

17. The method of claim 16, wherein the reference is healthy tissue.

18. The method of claim 16, wherein the reference is the target in which the flow rate of the fluid and the concentration of one or more analytes have been previously been quantified.

19. The method of claim 1, wherein performing angiography comprises performing angiography on the target with fast scanning and wide field imaging using narrow band illumination.

* * * * *